United States Patent
Hirayama

(10) Patent No.: US 10,571,671 B2
(45) Date of Patent: Feb. 25, 2020

(54) SURGICAL CONTROL DEVICE, CONTROL METHOD, AND IMAGING CONTROL SYSTEM

(71) Applicant: SONY CORPORATION, Tokyo (JP)

(72) Inventor: Tomoyuki Hirayama, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 12 days.

(21) Appl. No.: 15/122,550

(22) PCT Filed: Mar. 20, 2015

(86) PCT No.: PCT/JP2015/001585
§ 371 (c)(1),
(2) Date: Aug. 30, 2016

(87) PCT Pub. No.: WO2015/151447
PCT Pub. Date: Oct. 8, 2015

(65) Prior Publication Data
US 2017/0068081 A1    Mar. 9, 2017

(30) Foreign Application Priority Data

Mar. 31, 2014  (JP) ................. 2014-071169

(51) Int. Cl.
*G02B 21/00*    (2006.01)
*A61B 90/25*    (2016.01)
(Continued)

(52) U.S. Cl.
CPC ...... *G02B 21/0012* (2013.01); *A61B 1/00149* (2013.01); *A61B 1/00188* (2013.01);
(Continued)

(58) Field of Classification Search
CPC .............. G02B 21/0012; G02B 21/365; G02B 21/025; G06F 3/013; A61B 90/25;
(Continued)

(56) References Cited

U.S. PATENT DOCUMENTS 5,276,785 A  *  1/1994  Mackinlay .......... G06F 3/04815
                                                         345/427
5,836,869 A     11/1998  Kudo et al.
(Continued)

FOREIGN PATENT DOCUMENTS

JP       6-75617        3/1994
JP       07299027 A     11/1995
(Continued)

OTHER PUBLICATIONS

International Search Report dated Jul. 27, 2015 in PCT/JP2015/001585.
(Continued)

*Primary Examiner* — Tracy Y. Li
(74) *Attorney, Agent, or Firm* — Xsensus LLP

(57) ABSTRACT

A surgical control device that includes circuitry that changes an imaging viewpoint of a surgical imaging device in order to maintain a substantially constant distance between a focal point of an object and the surgical imaging device that images the object, based on a first instruction of a user and position information acquired by an acquisition unit implemented by circuitry configured to acquire position information indicating a position of the focal point of the object.

10 Claims, 16 Drawing Sheets

(51) Int. Cl.
    *A61B 1/00*     (2006.01)
    *G02B 21/02*     (2006.01)
    *G02B 21/36*     (2006.01)
    *G06F 3/01*     (2006.01)
    *A61B 90/50*     (2016.01)
    *A61B 90/00*     (2016.01)
    *A61B 34/20*     (2016.01)

(52) U.S. Cl.
    CPC ............ *A61B 90/25* (2016.02); *G02B 21/025* (2013.01); *G02B 21/365* (2013.01); *G06F 3/013* (2013.01); *A61B 90/50* (2016.02); *A61B 2034/2048* (2016.02); *A61B 2090/368* (2016.02); *A61B 2090/502* (2016.02)

(58) Field of Classification Search
    CPC ............ A61B 1/00149; A61B 1/00188; A61B 90/50; A61B 2090/368; A61B 2034/2048; A61B 2090/502
    See application file for complete search history.

(56) References Cited

U.S. PATENT DOCUMENTS

| | | | | |
|---|---|---|---|---|
| 6,388,707 | B1 * | 5/2002 | Suda | H04N 5/23212 348/333.03 |
| 7,883,415 | B2 * | 2/2011 | Larsen | A63F 13/10 345/7 |
| 9,767,608 | B2 | 9/2017 | Lee et al. | |
| 2004/0001110 | A1 * | 1/2004 | Khan | G06F 3/04815 715/848 |
| 2007/0166027 | A1 * | 7/2007 | Misawa | G03B 17/02 396/529 |
| 2007/0236514 | A1 * | 10/2007 | Agusanto | A61B 1/00193 345/646 |
| 2008/0033240 | A1 * | 2/2008 | Hoffman | A61B 90/36 600/109 |
| 2009/0245600 | A1 * | 10/2009 | Hoffman | A61B 1/00039 382/128 |
| 2010/0228265 | A1 * | 9/2010 | Prisco | B25J 9/1689 606/130 |
| 2015/0062293 | A1 * | 3/2015 | Cho | H04N 5/23238 348/39 |
| 2015/0173846 | A1 | 6/2015 | Schneider et al. | |
| 2015/0198797 | A1 * | 7/2015 | Andre | A61B 5/7425 348/80 |

FOREIGN PATENT DOCUMENTS

| | | |
|---|---|---|
| JP | 08071072 A | 3/1996 |
| JP | 10127565 A | 5/1998 |
| JP | 10-315166 | 12/1998 |
| JP | 2005-66080 | 3/2005 |
| JP | 2008-67218 | 8/2008 |
| JP | 2013-180185 A | 9/2013 |
| JP | 2015192697 A | 11/2015 |
| KR | 20140112207 A | 9/2014 |
| WO | WO 03/002011 A1 | 1/2003 |
| WO | WO 2014/037953 A2 | 3/2014 |

OTHER PUBLICATIONS

Office Action dated Apr. 3, 2018 in corresponding Japanese Patent Application No. 2014-071169, 2 pages.
Office Action dated Apr. 3, 2018 in corresponding Japanese Patent Application No. 2014-071169, 5 pages.
Japanese Office Action dated May 14, 2019, issued in corresponding Japanese Patent Application No. 2018-126831, 8 pages.
Office Action dated Sep. 5, 207 in Japanese Petent Application No. 2014-071169.

\* cited by examiner

SURGICAL CONTROL DEVICE, CONTROL METHOD, AND IMAGING CONTROL SYSTEM

TECHNICAL FIELD

The present disclosure relates to a surgical control device, a control method, and an imaging control system, and particularly to a surgical control device, a control method, and an imaging control system by which a focused image with an imaging angle intended by a surgeon can be obtained.

CROSS REFERENCE TO RELATED APPLICATIONS

This application claims the benefit of Japanese Priority Patent Application JP 2014-071169 filed on Mar. 31, 2014, the entire contents of which are incorporated herein by reference.

BACKGROUND ART

In recent years, a medical observation system has been proposed, in which a point locking point is set independently from the setting of a focus position based on the measured data of the three dimensional shape of a portion to be observed (refer to PTL 1).

In addition, in a general surgical endoscopic observation, an endoscopist other than a surgeon moves the position of an endoscope in order to obtain a focused image of an observation target. Accordingly, the intentions of the surgeon and the operator of the endoscope sometimes do not match, and thus, there are cases where it is difficult to obtain a focused image of the observation target intended by the surgeon. A case where the surgeon directly operates the endoscope can be considered. However, in this case, the surgeon has to release the surgical instrument such as forceps held with both hands of the surgeon during operation, and thus, the surgical operation efficiency deteriorates.

CITATION LIST

Patent Literature

PTL 1: Japanese Unexamined Patent Application Publication No. 2013-180185

SUMMARY OF INVENTION

Technical Problem

Not only is an imaging target but also an imaging angle is important for a surgeon, and it is desirable for the surgeon to obtain a focused image with an imaging angle intended by the surgeon.

The present disclosure is to provide an imaging control system by which a focused image with the imaging angle intended by the surgeon can be obtained.

Solution to Problem

A surgical control device according to a first embodiment of the present disclosure includes: circuitry configured to change an imaging viewpoint of a surgical imaging device in order to maintain a substantially constant distance between a focal point of an object and the surgical imaging device that images the object, based on a first instruction of a user and position information acquired by an acquisition unit implemented by circuitry configured to acquire position information indicating a position of the focal point of the object.

A control method according to a first embodiment of the present disclosure correspond to the control device according to the first embodiment of the present disclosure.

According to the first embodiment of the present disclosure, the position information indicating the position of the focal point of the object is acquired, and imaging viewpoint of a surgical imaging device is changed in order to maintain a substantially constant distance between a focal point of an object and the surgical imaging device that images the object based on the first movement of the user and the position information.

An imaging control system according to a second embodiment of the present disclosure includes: an surgical imaging device that images an object, and a control device. The control device includes: circuitry configured to change an imaging viewpoint of a surgical imaging device in order to maintain a substantially constant distance between a focal point of an object and the surgical imaging device that images the object, based on an instruction of a user and position information acquired by an acquisition unit implemented by circuitry configured to acquire position information indicating a position of the focal point of the object.

According to the second embodiment of the present disclosure, the surgical imaging device images the object, the control device acquires the position information indicating the position of the focal point of the object, and changes the imaging viewpoint of a surgical imaging device in order to maintain a substantially constant distance between a focal point of an object and the surgical imaging device that images the object based on the first movement of the user and the position information.

Advantageous Effects of Invention

According to the first and second embodiments of the present disclosure, it is possible to control the imaging. In addition, according to the first and second embodiments of the present disclosure, it is possible to obtain a focused image with an imaging angle intended by a surgeon.

The effects described here are not necessarily limited, but any effects described in the present disclosure may be advantageous.

DESCRIPTION OF EMBODIMENTS

Hereinafter, a premise of the present disclosure and the embodiments of the present disclosure (hereafter, referred to as an embodiment) will be described. The description will be performed in the following order.

1. First embodiment: image processing device (FIGS. 1 to 10D)
2. Second embodiment: image processing system (FIG. 11)
3. Third embodiment: image processing system (FIGS. 12 to 15)
4. Fourth embodiment: computer (FIG. 16)

<First Embodiment>

(Description of an Overview of a Medical Observation System)

Figure 1:
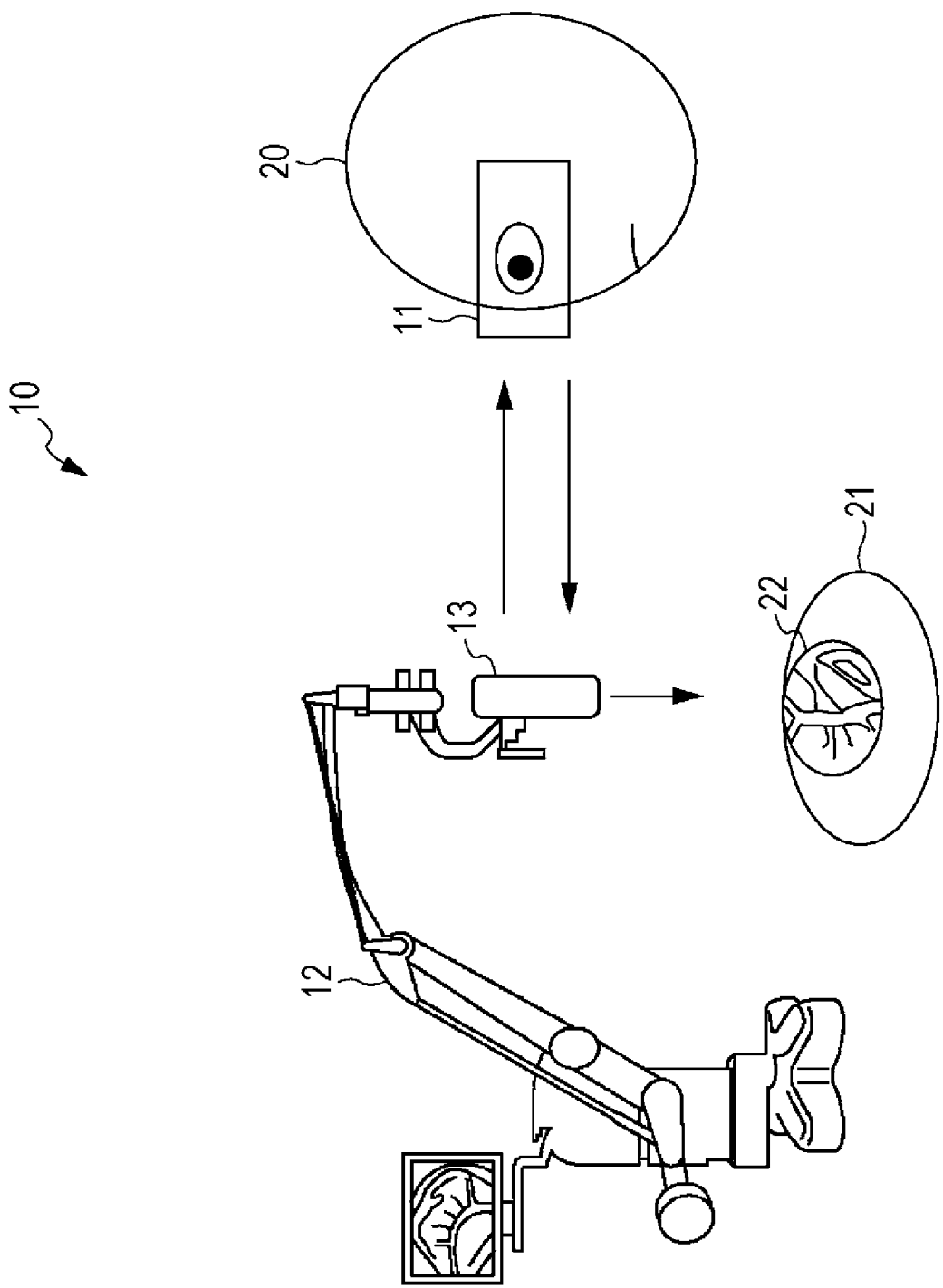
FIG. 1 is a diagram explaining an overview of a medical observation system in a first embodiment as an imaging control system to which the present disclosure is applied.

FIG. 1 is a diagram explaining an overview of a medical observation system in a first embodiment as an imaging control system to which the present disclosure is applied.

A medical observation system 10 is configured to include a head mount display 11, an electric arm 12, and a video microscope 13. A surgeon 20 as a user changes an imaging angle of the video microscope 13 by wearing the head mount display 11, looking at an image imaged by the video microscope 13 for surgical operation and displayed on the head mount display 11, and tilting the head vertically or horizontally.

Specifically, the head mount display 11 of the medical observation system 10 displays the image transmitted from the video microscope 13, in which an observation target 22 of a patient 21 is imaged as an object. At this time, the head mount display 11 detects a line-of-sight of the surgeon 20, and transmits gazing point position information that indicates a two-dimensional position of a gazing point of the surgeon 20 in the imaged image displayed, to the video microscope 13. In addition, the head mount display 11 (detection device) detects an angular velocity that indicates a vertical and horizontal head movement of the surgeon 20, and transmits the detection result to the electric arm 12.

The electric arm 12 holds the video microscope 13 so as to be able to freely move and turn in the three dimensional directions. The electric arm 12 changes the three dimensional position of the video microscope 13 according to the operation of the surgeon or an endoscopist. For example, the surgeon or an endoscopist manually changes the three dimensional position of the video microscope 13 such that the observation target 22 is imaged by the video microscope 13 by moving the electric arm 12.

In addition, the electric arm 12 acquires distance information transmitted from the video microscope 13, which indicates a distance from the video microscope 13 to the object in the focus area. The electric arm 12 acquires focus area information (position information) that indicates a three dimensional position of the object in the focus area based on the distance information and arm angle information of the electric arm 12. The electric arm 12 acquires the detection result (angular velocity) transmitted from the head mount display 11. The electric arm 12 changes the imaging angle of the video microscope 13 without changing the distance between the video microscope 13 and the gazing point, based on the acquired detection result and the focus area information.

At the time of starting the imaging, the video microscope 13 (imaging device) takes a predetermined area such as a center area in the imaged image as the focus area, and performs the imaging so as to focus on the focus area. In addition, the video microscope 13, in a case of a time other than starting the imaging, takes the position indicated by the gazing point position information transmitted from the head mount display 11 as the focus area, and performs the imaging so as to focus on the focus area.

The video microscope 13 transmits the imaged image obtained as result of imaging to the head mount display 11. In addition, the video microscope 13 detects the distance from the video microscope 13 to the object in the focus area, and transmits the distance information indicating the distance to the electric arm 12.

(Configuration Example of the Medical Observation System)

Figure 2:
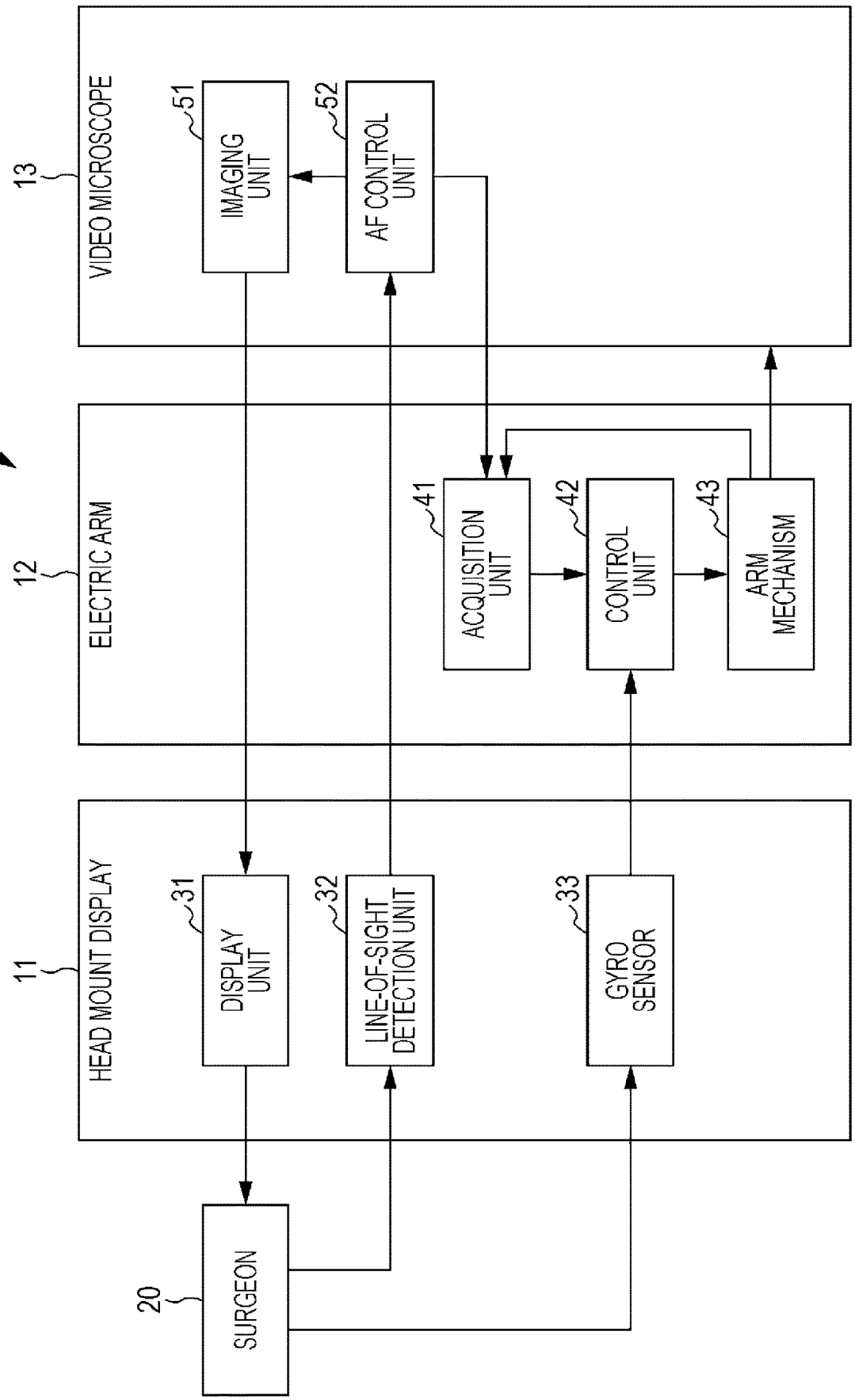
FIG. 2 is a block diagram illustrating a configuration example of the medical observation system in FIG. 1.

FIG. 2 is a block diagram illustrating a configuration example of the medical observation system 10 in FIG. 1.

As illustrated in FIG. 2, the head mount display 11 includes a display unit 31, a line-of-sight detection unit 32, and a gyro sensor 33.

The display unit 31 of the head mount display 11 displays the imaged image transmitted from the video microscope 13. The line-of-sight detection unit 32, for example, is configured with an infrared light source and an infrared camera, and detects the line-of-sight of the surgeon 20 from the infrared image of a pupil of the surgeon 20. The line-of-sight detection unit 32 generates the gazing point position information with the point in the imaged image displayed, to which the surgeon 20 gazes as the gazing point, based on the detection result. The line-of-sight detection unit 32 transmits the gazing point position information to the video microscope 13.

The gyro sensor 33 (movement detection unit) is a biaxial gyro sensor, and detects the angular velocity of the vertical and horizontal head turning of the surgeon 20. The gyro sensor 33 transmits the detection result to the electric arm 12.

Here, the head mount display 11 includes the gyro sensor 33 in order to detect the head movement of the surgeon 20, but may include any device other than the gyro sensor 33 as long as the device is capable of detecting the head movement. For example, the head mount display 11 can include a camera that images the operation site instead of the gyro sensor 33, and can detect the head movement of the surgeon 20 from the movement of the imaged image. In addition, in the medical observation system 10, a fixed camera that images the head of the surgeon 20 may be installed at the outside of the head mount display 11, and the head movement of the surgeon 20 may be detected based on the imaged image.

The electric arm 12 (control device) includes an acquisition unit 41, a control unit 42, and an arm mechanism 43.

The acquisition unit 41 of the electric arm 12 acquires the distance information transmitted from the video microscope 13. In addition, the acquisition unit 41 acquires arm angle information that indicates an angle of the arm mechanism 43 from the arm mechanism 43. The acquisition unit 41 acquires the focus area information based on the distance information and the arm angle information, and supplies the focus area in formation to the control unit 42.

The control unit 42 acquires the detection result transmitted from the gyro sensor 33. The control unit 42 controls the arm mechanism 43 so as to change the imaging angle of the video microscope 13 without changing the distance between the video microscope 13 and the gazing point, based on the acquired detection result and the focus area information supplied from the acquisition unit 41. That is, the control unit 42 controls the arm mechanism 43 such that the video microscope 13 turns with the position indicated by the focus area information as the center position of turning.

The arm mechanism 43 (holding unit) holds the video microscope 13 so as to freely move and turn in the three dimensional directions. The arm mechanism 43 changes the imaging angle of the video microscope 13 by causing the video microscope 13 to move and to turn based on the control from the control unit 42. In addition, the arm mechanism 43 causes the video microscope 13 to move to an arbitrary three dimensional position according to the operation of the surgeon 20 and the endoscopist.

The video microscope 13 (imaging device) includes an imaging unit 51 and an AF control unit 52.

The imaging unit 51 of the video microscope 13 performs the imaging based on the focus control of the AF control unit 52, and transmits the imaged image obtained as a result of imaging to the head mount display 11.

The AF control unit 52, when the imaging starts, sets the predetermined area such as the center area of the imaged image as the focus area. In addition, in a case of the time other than starting imaging, the AF control unit 52 sets the position indicated by the gazing point information transmitted from the head mount display 11 as the focus area.

The AF control unit 52 controls the focusing of the imaging unit 51 such that the image focuses on the focus area by a detection method such as a contrast detection system or a phase difference detection system. In association with this, the AF control unit 52 detects the distance between the video microscope 13 and the object in the focus area, and transmits the distance information indicating the detected distance to the electric arm 12.

(Example of Gazing Point)

Figure 3:
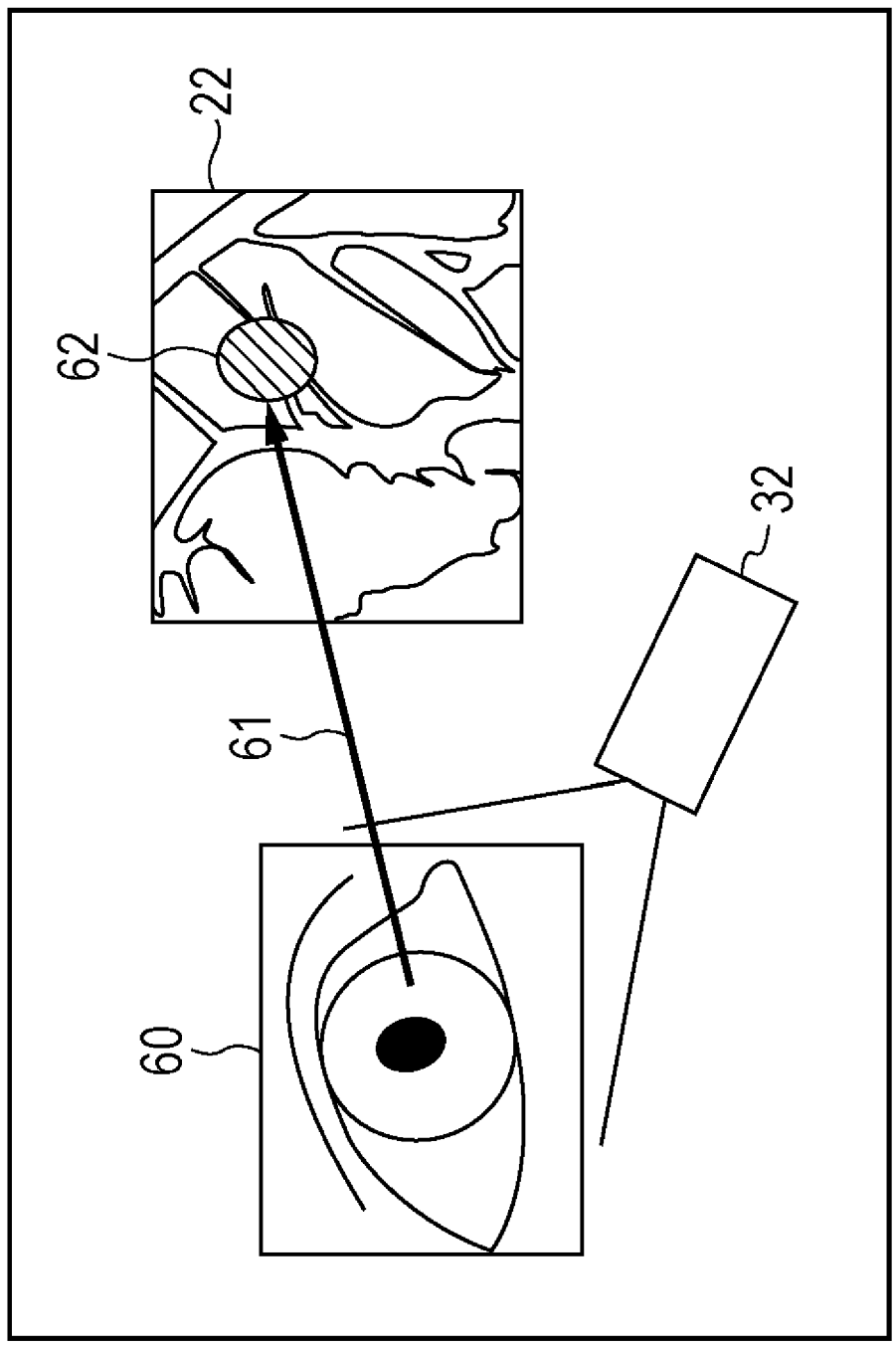
FIG. 3 is a diagram illustrating an example of a gazing point.

FIG. 3 is a diagram illustrating an example of the gazing point. As illustrated in FIG. 3, the line-of-sight detection unit 32 detects a line-of-sight 61 of the surgeon 20 from an infrared image 60 of the pupil of the surgeon 20. The line-of-sight detection unit 32 determines the position of an imaged image displayed in the observation target 22 corresponding to the line-of-sight 61 of the surgeon 20 as the gazing point 62 based on the detection result.

(Example of the Head Movement of the Surgeon)

Figure 4:
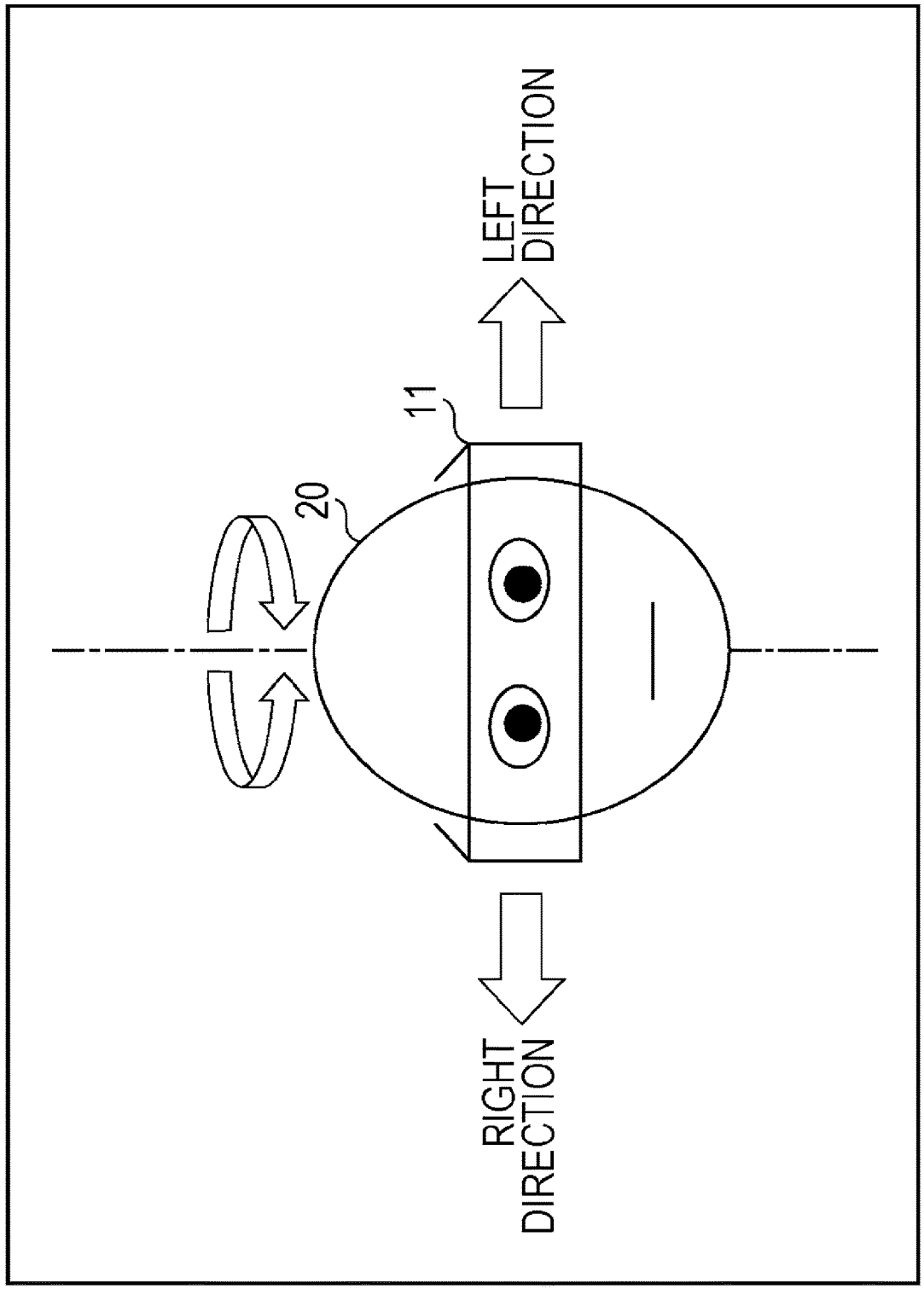
FIG. 4 is a diagram illustrating an example of a head movement of a surgeon when an imaging angle is changed.
Figure 5:
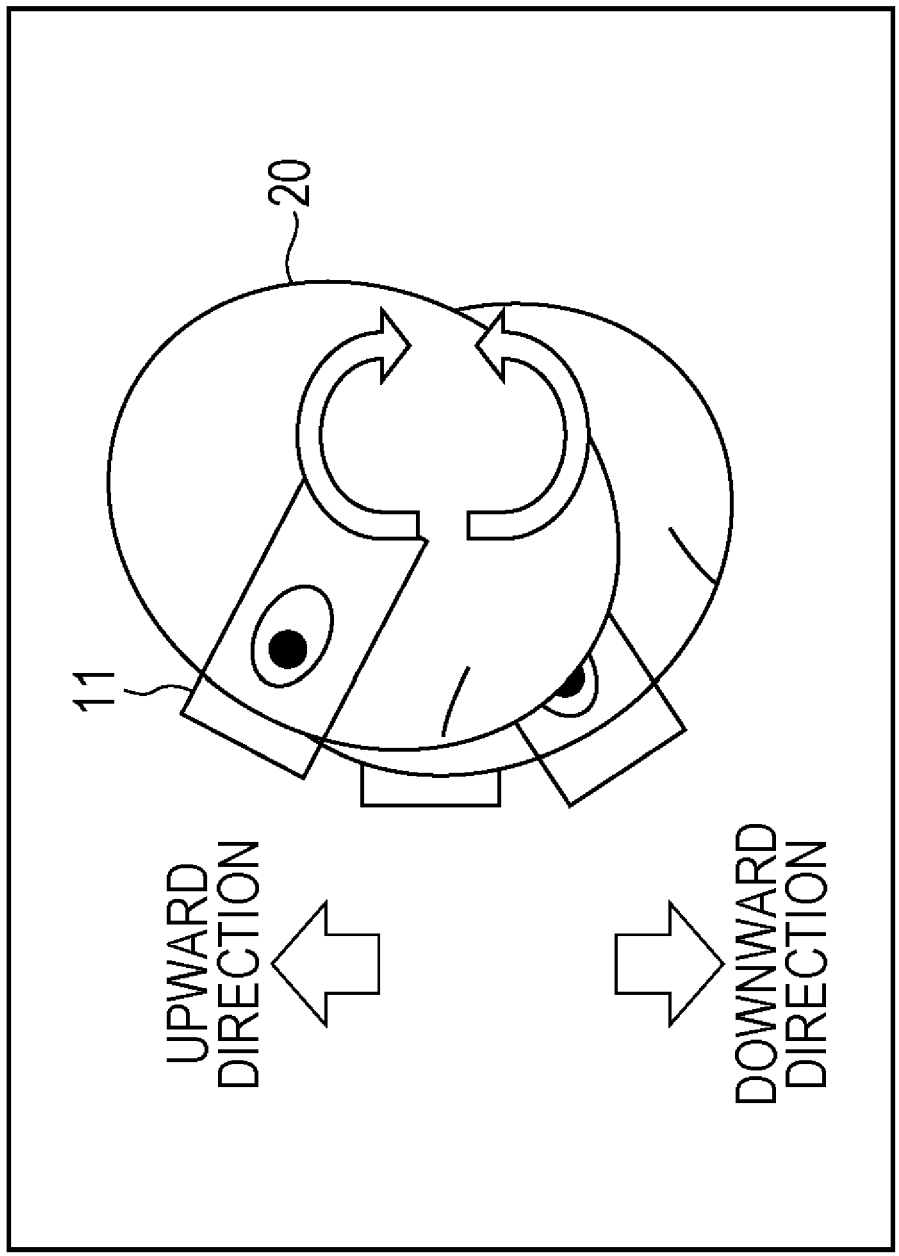
FIG. 5 is a diagram illustrating an example of a head movement of a surgeon when an imaging angle is changed.

FIG. 4 and FIG. 5 are diagrams illustrating examples of a head movement of a surgeon 20 when an imaging angle of the video microscope 13 is changed.

As illustrated in FIG. 4, the surgeon 20, when the imaging angle of the video microscope 13 is changed, in a state in which the head mount display 11 is mounted, turns his/her head in a horizontal direction, or turns his/her head in a vertical direction as illustrated in FIG. 5. In addition, the surgeon 20 may turn the head in a horizontal direction and in a vertical direction at the same time.

The angular velocity of the head of the surgeon 20 in the horizontal direction and the angular velocity in the vertical direction are detected by the gyro sensor 33.

(Example of a Relationship Between the Head Movement of the Surgeon and the Imaging Angle)

Figure 6:
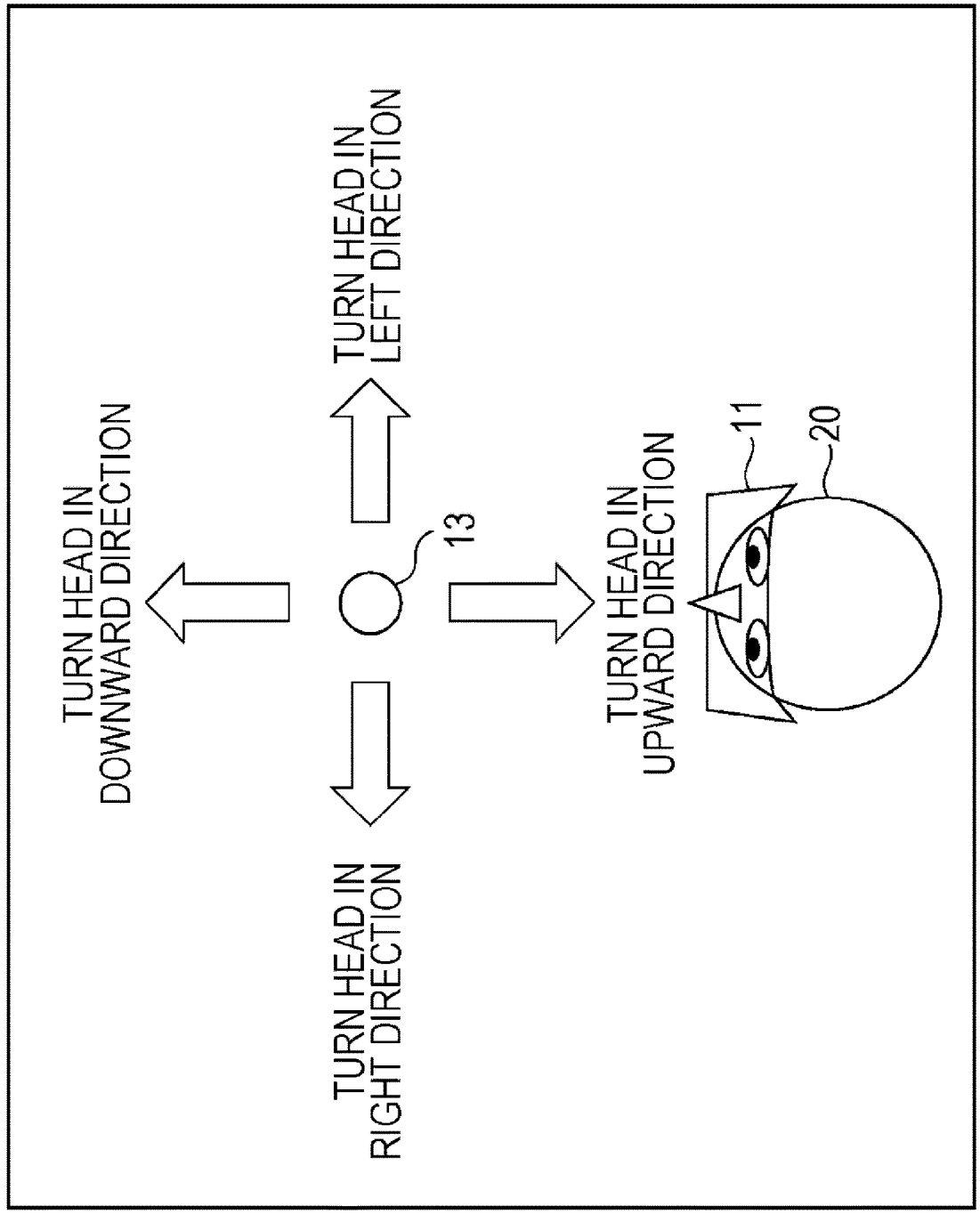
FIG. 6 is a diagram illustrating an example of a relationship between the head movement of the surgeon and the imaging angle.

FIG. 6 is a diagram illustrating an example of a relationship between the head movement of the surgeon 20 and the imaging angle, and is a diagram of the surgeon 20 wearing the head mount display 11 and the video microscope 13, viewed from the top.

As illustrated in FIG. 6, when the surgeon 20 wearing the head mount display 11 looks at the gazing point and turns his/her head in the left direction, the video microscope 13 turns in the right direction with the gazing point as the center. As a result, the imaging unit 51 of the video microscope 13 images the gazing point from the right direction.

On the other hand, when the surgeon 20 wearing the head mount display 11 looks at the gazing point and turns his/her head in the right direction, the video microscope 13 turns in the left direction with the gazing point as the center. As a result, the imaging unit 51 of the video microscope 13 images the gazing point from the left direction.

In addition, when the surgeon 20 wearing the head mount display 11 looks at the gazing point and turns his/her head in the upward direction, the video microscope 13 turns in the downward direction with the gazing point as the center. As a result, the imaging unit 51 of the video microscope 13 images the gazing point from the downward direction.

On the other hand, when the surgeon 20 wearing the head mount display 11 looks at the gazing point and turns his/her head in the downward direction, the video microscope 13 turns in the upward direction with the gazing point as the center. As a result, the imaging unit 51 of the video microscope 13 images the gazing point from the upward direction.

The relationship between the head movement of the surgeon 20 and the imaging angle is not limited to the example in FIG. 6. For example, the direction of the head turning of the surgeon 20 may be the same as the direction of turning of the video microscope 13.

(Description of a Movement of the Video Microscope)

Figure 7:
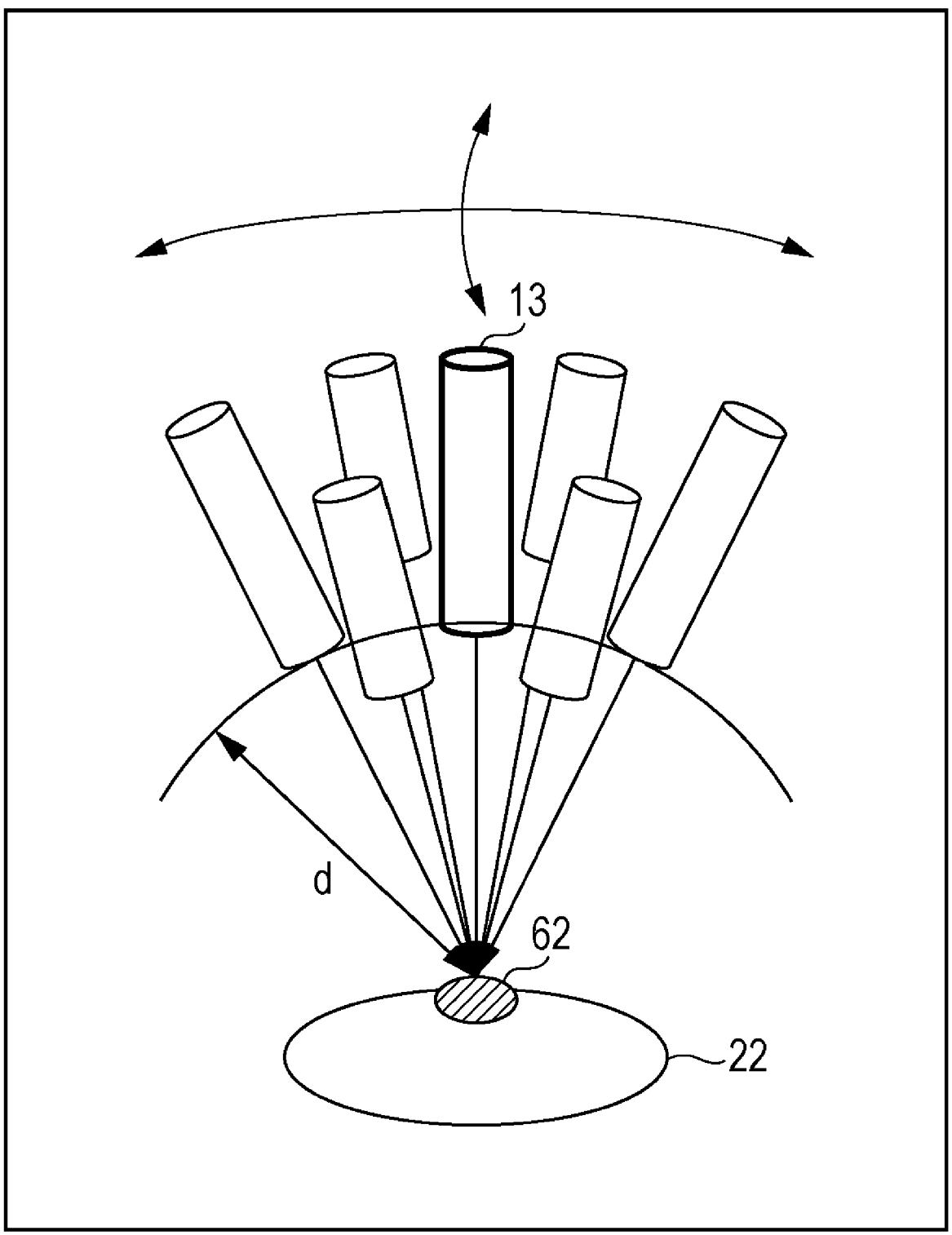
FIG. 7 is a diagram explaining a movement of a video microscope.
Figure 8:
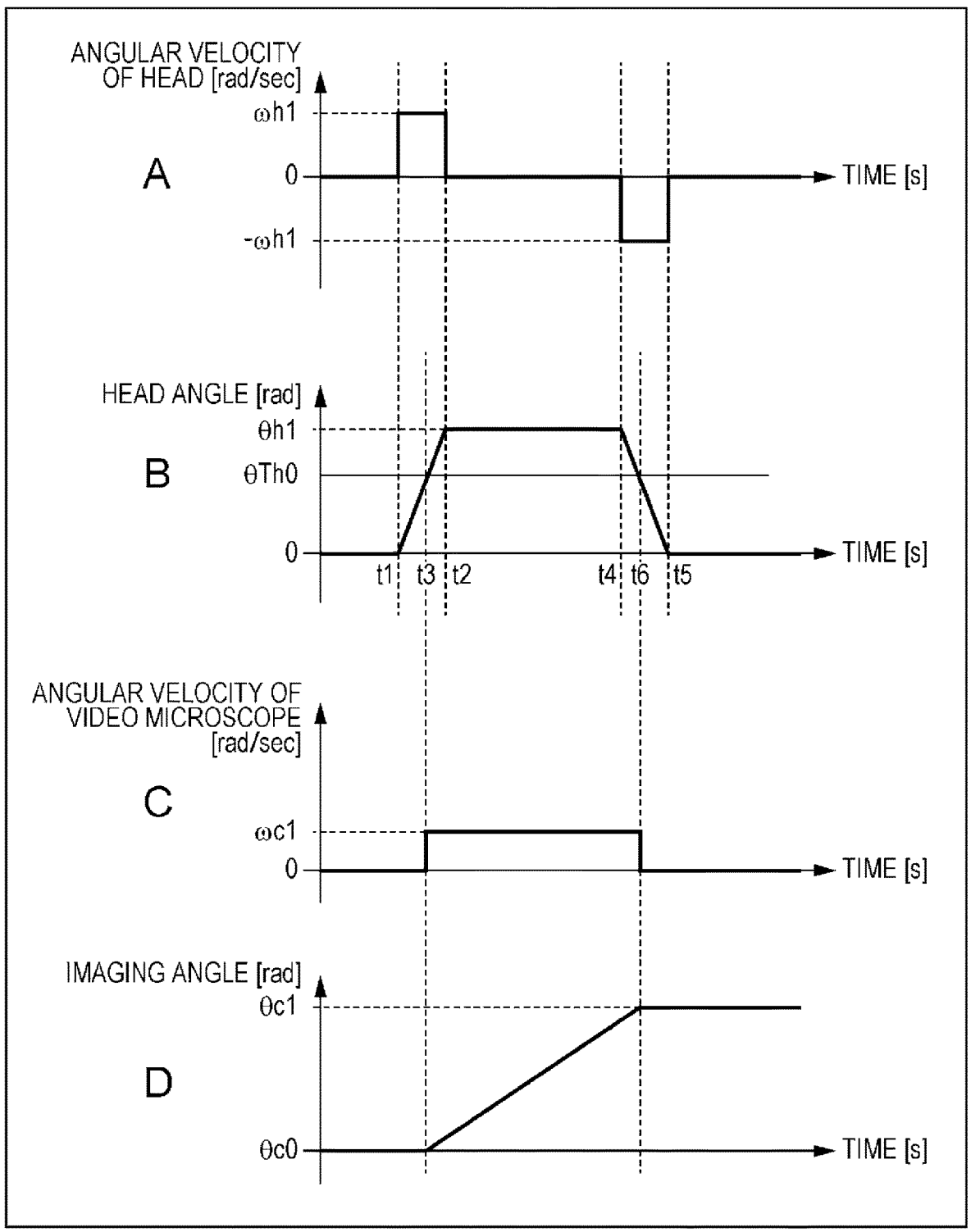
FIG. 8 is a diagram illustrating an example of a temporal change of an angular velocity of the head turning and the imaging angle.

FIG. 7 is a diagram explaining a movement of a video microscope 13 according to the head movement of the surgeon 20.

As illustrated in FIG. 7, the video microscope 13 turns by the arm mechanism 43 of the electric arm 12 with the gazing point 62 of the observation target 22 as the center according to the head movement of the surgeon 20. In this way, the distance d between the lower surface of the video microscope 13 and the gazing point 62 becomes constant regardless of the movement of the video microscope 13. As a result, even in a case where the imaging angle is changed, it is possible to maintain the focused state.

(Example of a Temporal Change of the Angular Velocity of the Head and the Imaging Angle)

FIGS. 8A to 8D are diagrams illustrating an example of a temporal change of an angular velocity of the head turning and the imaging angle of the video microscope 13 detected by the gyro sensor 33.

In the example in FIGS. 8A to 8D, in order to perform the imaging from the right direction, the surgeon 20 turns his/her head to the left direction from the point in time t1 at a constant velocity and stops turning at the point in time t2 when the head direction reaches a predetermined direction. In this way, as illustrated in FIG. 8A, the gyro sensor 33 detects the angular velocity $\omega h1$ as the horizontal angular velocity of the head of the surgeon 20 between the point in time t1 and the point in time t2, and transmits the angular velocity $\omega h1$ to the control unit 42.

The control unit 42 acquires the angular velocity $\omega h1$ from the point in time t1 to the point in time t2 from the gyro sensor 33. The control unit 42 measures the horizontal head angle of the surgeon 20 at the present point in time by integrating the angular velocity acquired from the point in time t1 to the present point in time. The angle measured in this way increases from zero to $\theta h1$ with a predetermined slope from the point in time t1 to the point in time t2 as illustrated in FIG. 8B.

As illustrated in FIG. 8C, the control unit 42 controls the arm mechanism 43 in the point in time t3 when the measured angle exceeds the threshold value $\theta Th0 (\theta Th0 < \theta h1)$, and starts the turning of the video microscope 13 at the angular velocity $\omega c1$ in the right direction.

The surgeon 20, after the point in time t2, does not move his/her head until the imaging angle of the video microscope 13 is close to the desired imaging angle, and at the point in time t4, when the imaging angle of the video microscope 13 is close to the desired imaging angle, turns his/her head at the constant velocity in the right direction. As a result, at the point in time t5, the head of the surgeon 20 returns to the original position and then, the surgeon 20 stops the turning of his/her head.

In this way, as illustrated in FIG. 8A, the gyro sensor 33 detects the angular velocity 0 from the point in time t2 to the point in time t4, and transmits the angular velocity 0 to the control unit 42. In addition, the gyro sensor 33 detects the angular velocity $-\omega h1$ from the point in time t4 to the point in time t5, and transmits the angular velocity $-\omega h1$ to the control unit 42.

The control unit 42 acquires the angular velocity 0 from the gyro sensor 33 from the point in time t2 to the point in time t4. The control unit 42 measures the horizontal angle of the head of the surgeon 20 at the present point in time by integrating the angular velocity acquired from the point in time t1 to the present point in time. The angle measured in this way is the angle $\theta h1$ from the point in time t2 to the point in time t4 as illustrated in FIG. 8B.

In addition, the control unit 42 acquires the angular velocity $-\omega h1$ from the gyro sensor 33 from the point in time t4 to the point in time t5. The control unit 42 measures the horizontal angle of the head of the surgeon 20 at the present point in time by integrating the angular velocity acquired from the point in time t1 to the present point in time. The angle measured in this way decreases from $\theta h1$ to zero with a predetermined slope from the point in time t4 to the point in time t5 as illustrated in FIG. 8B.

As illustrated in FIG. 8C, in the point in time t6 when the measured angle becomes equal to or less than the threshold value $\theta Th0$, the control unit 42 controls the arm mechanism 43, makes the angular velocity of the turning of the video microscope 13 in the right direction started at the point in time t3 to be zero, and stops the turning.

In this way, the video microscope 13 turns in the right direction at the angular velocity $\omega c1$ from the point in time t3 to the point in time t6. As a result, as illustrated in FIG. 8D, the imaging angle increases from the imaging angle $\theta c0$ which is the imaging angle before the horizontal turning of the head to the imaging angle $\theta c1$ at the angular velocity $\omega c1$ from the point in time t3 to the point in time t6. The imaging angle after the point in time t6 is fixed to the imaging angle $\theta c1$.

As described above, in the medical observation system 10, by using the turning of the head of the surgeon 20 in the left direction as a trigger point, the imaging angle is changed by the turning of the video microscope 13 in the right direction corresponding to the direction of the head turning. After that, by using the turning of the head of the surgeon 20 in the right direction reverse to the previous direction as a trigger point, the video microscope 13 stops the turning, and the imaging angle is fixed.

In FIGS. 8A to 8D, the case where the surgeon 20 turns his/her head in the left direction is described. However, in a case where the surgeon turns his/her head in the right direction also, the processing is the same except the point that the direction of the turning of the video microscope 13 is a left direction. In addition, regarding the case where the surgeon 20 vertically moves his/her head, the processing is same as the case where the head turns horizontally except the point that the imaging angle is a vertical angle. In a case where the surgeon 20 turns his/her head both in the vertical direction and the horizontal direction simultaneously, the processes in the cases where the head turns in the horizontal direction and in the vertical direction are performed simultaneously.

(Description of the Processing of the Medical Observation System)

Figure 9:
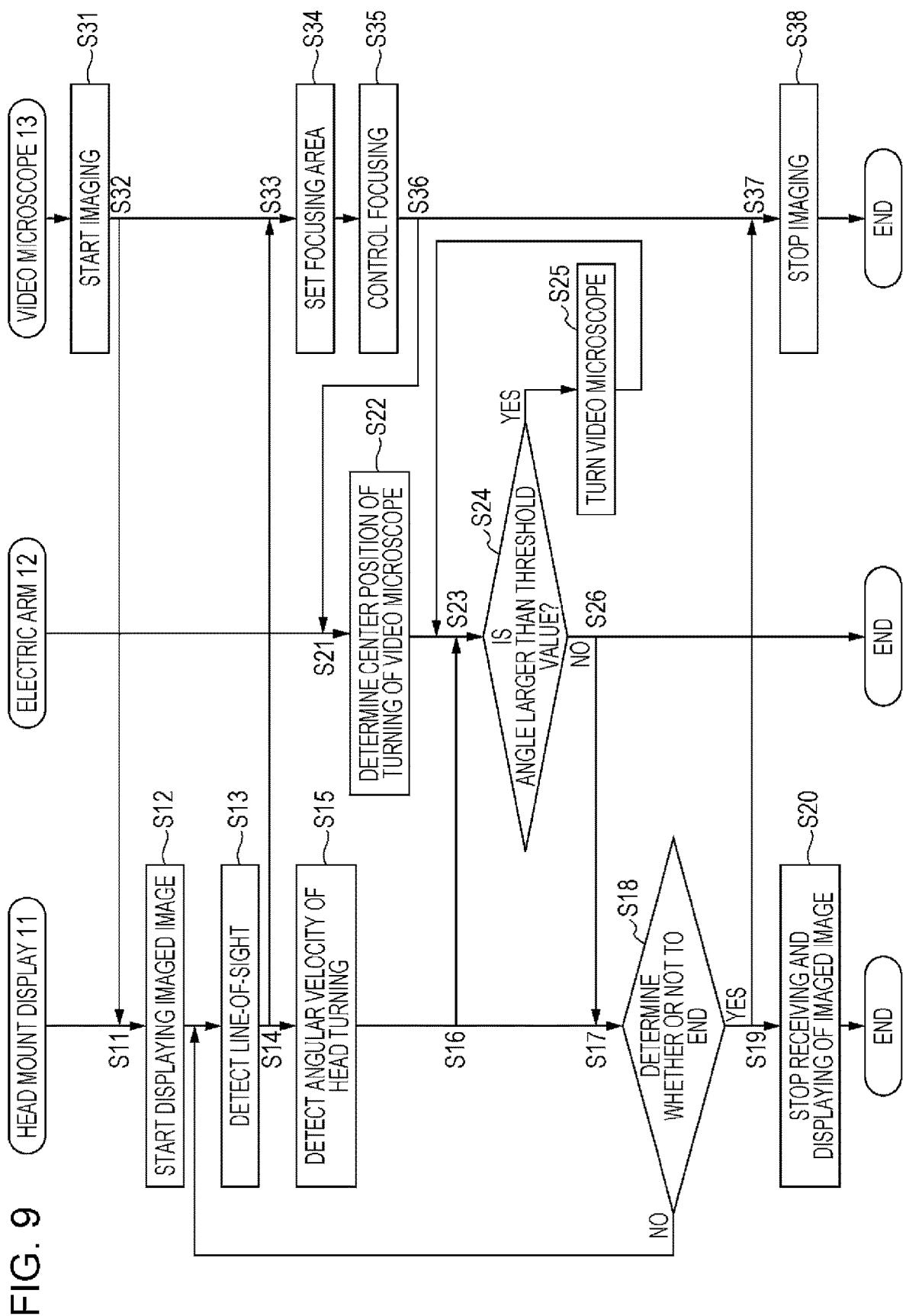
FIG. 9 is a flow chart explaining imaging angle control processing of the medical observation system in FIG. 1.
Figure 10:
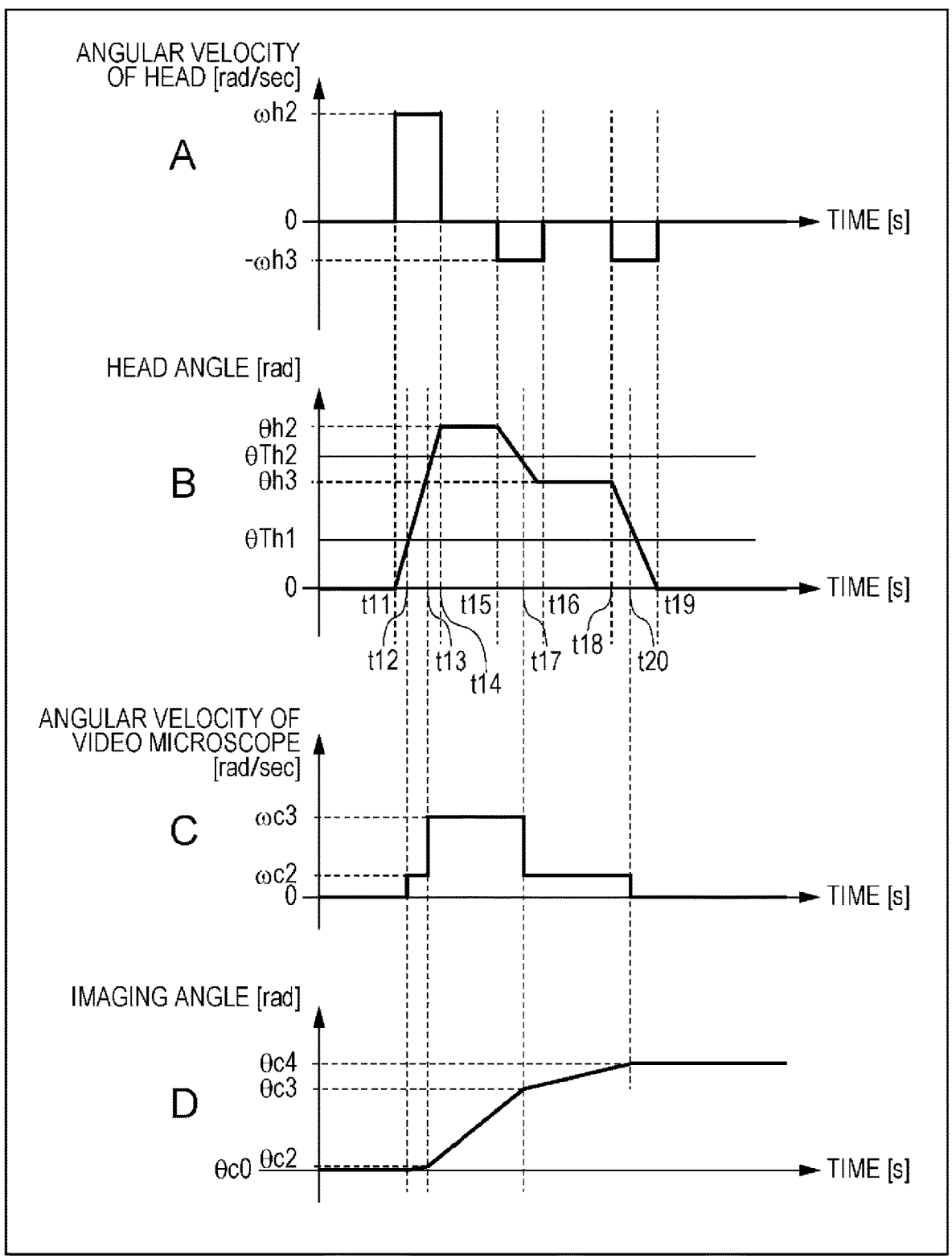
FIG. 10 is a diagram illustrating another example of a temporal change of an angular velocity of the head turning and the imaging angle.

FIG. 9 is a flow chart explaining imaging angle control processing of the medical observation system 10 in FIG. 1.

In STEP S31 in FIG. 9, the imaging unit 51 of the video microscope 13 starts imaging of the observation target 22. The imaging is controlled by the AF control unit 52 such that the image is focused on the focus area. The initial value of the focus area is, for example, the center area in the imaged image. In STEP S32, the imaging unit 51 starts the transmission of the imaged image obtained as a result of imaging started in STEP S31 to the head mount display 11.

In STEP S11, the display unit 31 of the head mount display 11 starts receiving the imaged image transmitted from the imaging unit 51. In STEP S12, the display unit 31 starts displaying the received imaged image. The surgeon 20 gazes at the desired position in the imaged image displayed. At this time, the surgeon 20, in a case where the imaging angle is changed, vertically and horizontally turns his/her head according to the imaging angle, and in a case where the imaging angle reaches the desired angle, then turns his/her head in the reverse direction, and then, returns his/her head to the original position.

In STEP S13, the line-of-sight detection unit 32 detects the line-of-sight of the surgeon 20. The line-of-sight detection unit 32, based on the detection result, generates the gazing point position information with the point at which the surgeon 20 gazes in the imaged image displayed, as the gazing point. In STEP S14, the line-of-sight detection unit 32 transmits the gazing point position information to the video microscope 13.

In STEP S33, the AF control unit 52 of the video microscope 13 acquires the gazing point position information transmitted from the line-of-sight detection unit 32. In STEP S34, the AF control unit 52 sets (updates) the position indicated by the gazing point position information as the focus area. The AF control unit 52 detects the distance between the video microscope 13 and the object in the focus area.

In STEP S35, the AF control unit 52 controls the focusing of the imaging unit 51 such that the image is focused on the focus area. In STEP S36, the AF control unit 52 detects the distance between the video microscope 13 and the object in the focus area, and transmits the distance information that indicates the detected distance to the electric arm 12.

In STEP S21, the acquisition unit 41 of the electric arm 12 acquires the distance information transmitted from the video microscope 13. The acquisition unit 41 acquires the focus area information and transmits the focus area information to the control unit 42 based on the acquired distance information and the arm angle information supplied from the arm mechanism 43. In STEP S22, the control unit 42 determines the position indicated by the focus area information supplied from the acquisition unit 41 to be the center position of the turning of the video microscope 13.

In STEP S15, the gyro sensor 33 of the head mount display 11 detects the angular velocity of the head turning of the surgeon 20 in the vertical and horizontal direction. In STEP S16, the gyro sensor 33 transmits the detection result to the electric arm 12.

In STEP S23, the control unit 42 of the electric arm 12 acquires the detection result transmitted from the gyro sensor 33. The processing in STEP S24 and STEP S25 is performed regarding the vertical head turning and the horizontal head turning respectively.

In STEP S24, the control unit 42 integrates the angular velocity of the head turning which is the acquired detection result, and determines whether the angle of the head turning obtained by the integration result is larger than the threshold value $\theta Th0$ or not. In a case where the angle of the head turning is larger than the threshold value $\theta Th0$ in STEP S24, that is, in a case where the surgeon 20 turns his/her head in the direction corresponding to the desired direction, the process proceeds to STEP S25.

In STEP S25, the control unit 42 controls the arm mechanism 43, and turns the video microscope 13 with the center position of turning determined in STEP S22 as the center of turning at the angular velocity $\omega c1$ in the direction corresponding to the direction of head turning. Then, the process returns to STEP S23.

On the other hand, in a case where the angle of the head is determined not to be larger than the threshold value $\theta Th0$ in STEP S24, that is, in a case where the surgeon 20 returns his/her head to the original position, or in case where the surgeon 20 does not turns his/her head, the process proceeds to STEP S26. In STEP S26, the electric arm 12 notifies the head mount display 11 that the turning of the video microscope 13 stops.

In STEP S17, the head mount display 11 receives the notification of the stop of the turning of the video microscope 13 from the electric arm 12. In STEP S18, the head mount display 11 determines whether or not to end the process according to the operation of an operation unit not illustrated, by the surgeon 20.

In a case where the process is determined not to end in STEP S18, the process returns to STEP S13 and repeats the subsequent processes.

On the other hand, in a case where the process is determined to end in STEP S18, in STEP S19, the head mount display 11 notifies the video microscope 13 that the process stops.

In STEP S37, the video microscope 13 receives the notification of the stop of the process from the head mount display 11. In STEP S38, the imaging unit 51 of the video microscope 13 stops imaging.

In STEP S20, the display unit 31 of the head mount display 11 stops the receiving and displaying of the imaged image transmitted from the imaging unit 51.

In the above description, one threshold value of the angle of the head is provided, and with the fact that the angle of the head exceeds the threshold value as a trigger point, the video microscope 13 turns at a predetermined angular velocity. However, two or more threshold values of the angle of the head may be provided. In this case, with the fact that the angle of the head exceeds the least threshold value as a trigger point, the video microscope 13 turns at a predetermined angular velocity, and with the fact that the angle of the head exceeds the other threshold values as trigger points, the angular velocity of the video microscope 13 is changed.

(Another Example of Temporal Change of the Angular Velocity of the Head and the Imaging Angle)

FIGS. 10A to 10D are diagrams illustrating another example of a temporal change of an angular velocity of the head detected by the gyro sensor 33 and the imaging angle of the video microscope 13 in a case where two threshold values of the angle of the head are provided.

Specifically, in the example in FIGS. 10A to 10D, in order to perform the imaging from the right direction, the surgeon 20 turns his/her head to the left direction from the point in time t11 at a constant velocity and stops turning at the point in time t14 when the head direction reaches a predetermined direction. At this time, as illustrated in FIG. 10A, the gyro sensor 33 detects the angular velocity $\omega h2$
as the horizontal angular velocity of the head of the surgeon 20 between the point in time t11 and the point in time t14, and transmits the angular velocity
$\omega h2$
to the control unit 42.

The control unit 42 acquires the angular velocity
$\omega h2$
from the point in time t11 till the point in time t14 from the gyro sensor 33. The control unit 42 measures the horizontal head angle of the surgeon 20 at the present point in time by integrating the angular velocity acquired from the point in time t11 to the present point in time. The angle measured in this way increases from zero to
$\theta h2$
with a predetermined slope from the point in time t11 to the point in time t14 as illustrated in FIG. 10B.

As illustrated in FIG. 10C, the control unit 42 controls the arm mechanism 43 in the point in time t12 when the measured angle exceeds the threshold value
$\theta Th1(\theta Th1 < \theta h2)$,
and starts the turning of the video microscope 13 at the angular velocity
$\omega c2$
in the right direction.

The control unit 42 controls the arm mechanism 43 in the point in time t13 when the measured angle exceeds the threshold value
$\theta Th2(\theta Th1 < \theta Th2 < \theta h2)$,
and changes the angular velocity of the turning of the video microscope 13 in the right direction to
$\omega c3$
from
$\omega c2 (\omega c2 < \omega c3)$.

In this way, the video microscope 13 turns at the angular velocity
$\omega c1$
in the right direction from the point in time t12 to the point in time t13. As a result, as illustrated in FIG. 10D, the imaging angle increases from
$\theta c0$
which is the imaging angle before the head horizontally turns to the imaging angle
$\theta c2$
at the angular velocity
$\omega c2$
from the point in time t12 to t13.

The surgeon 20, after the point in time t14, does not move his/her head until the imaging angle of the video microscope 13 is close to the desired imaging angle. At the point in time t15, when the imaging angle of the video microscope 13 is close to the desired imaging angle, the surgeon 20 turns his/her head at the constant velocity in the right direction, and stops the turning of his/her head at the point in time t16 when the head directs the predetermined direction.

In this way, as illustrated in FIG. 10A, the gyro sensor 33 detects the angular velocity 0 from the point in time t14 to the point in time t15, and transmits the angular velocity 0 to the control unit 42. In addition, the gyro sensor 33 detects the angular velocity
$-\omega h3$
from the point in time t15 to the point in time t16, and transmits the angular velocity
$-\omega h3$
to the control unit 42.

The control unit 42 acquires the angular velocity 0 from the gyro sensor 33 from the point in time t14 to the point in time t15. The control unit 42 measures the horizontal head angle of the surgeon 20 at the present point in time by integrating the angular velocity acquired from the point in time t11 to the present point in time. The angle measured in this way is the angle
$\theta h2$
from the point in time t14 to the point in time t15 as illustrated in FIG. 10B.

In addition, the control unit 42 acquires the angular velocity
$-\omega h3$
from the gyro sensor 33 from the point in time t15 to the point in time t16. The control unit 42 measures the horizontal head angle of the surgeon 20 at the present point in time by integrating the angular velocity acquired from the point in time t11 to the present point in time. The angle measured in this way decreases from
$\theta h2$
to
$\theta h3 (\theta Th1 < \theta h3 \leq \theta Th2)$
with a predetermined slope from the point in time t15 to the point in time t16 as illustrated in FIG. 10B.

As illustrated in FIG. 10C, the control unit 42 controls the arm mechanism 43 in the point in time t17 when the measured angle is equal to or smaller than the threshold value
$\theta Th2$,
and returns the angular velocity of the turning of the video microscope 13 to angular velocity
$\omega c2$
from the angular velocity
$\omega c3$ In this way, the video microscope 13 turns in the right direction at the angular velocity
$\omega c1$
from the point in time t13 to the point in time t17. As a result, as illustrated in FIG. 10D, the imaging angle increases from the imaging angle
$\theta c2$
to the imaging angle
$\theta c3$
at the angular velocity
$\omega c3$
from the point in time t13 to the point in time t17.

The surgeon 20, after the point in time t16, does not move his/her head until the imaging angle of the video microscope 13 is close to the desired imaging angle, and at the point in time t18, when the imaging angle of the video microscope 13 is close to the desired imaging angle, turns his/her head at the constant velocity in the right direction. As a result, at the point in time t19, the head of the surgeon 20 returns to the original position and then, the surgeon 20 stops the turning of his/her head.

In this way, as illustrated in FIG. 10A, the gyro sensor 33 detects the angular velocity 0 from the point in time t16 to the point in time t18, and transmits the angular velocity 0 to the control unit 42. In addition, the gyro sensor 33 detects the angular velocity
$-\omega h3$
from the point in time t18 to the point in time t19, and transmits the angular velocity
$-\omega h3$
to the control unit 42.

The control unit 42 acquires the angular velocity 0 from the gyro sensor 33 from the point in time t16 to the point in time t18. The control unit 42 measures the horizontal head angle of the surgeon 20 at the present point in time by integrating the angular velocity acquired from the point in time t11 to the present point in time. The angle measured in this way is the angle
θh3
from the point in time t16 to the point in time t18 as illustrated in FIG. 10B.

In addition, the control unit 42 acquires the angular velocity
ωh3
from the gyro sensor 33 from the point in time t18 to the point in time t19. The control unit 42 measures the horizontal head angle of the surgeon 20 at the present point in time by integrating the angular velocity acquired from the point in time t11 to the present point in time. The angle measured in this way decreases from
θh3
to zero with a predetermined slope from the point in time t18 to the point in time t19 as illustrated in FIG. 10B.

As illustrated in FIG. 10C, the control unit 42 controls the arm mechanism 43 in the point in time t20 when the measured angle becomes equal to or less than the threshold value
θTh1,
and makes the angular velocity of the turning of the video microscope 13 in the right direction changed at the point in time t17 to be zero to stop the turning.

In this way, the video microscope 13 turns in the right direction at the angular velocity
ωc2
from the point in time t17 to the point in time t20. As a result, as illustrated in FIG. 10D, the imaging angle increases from the imaging angle
θc3
to the imaging angle
θc4
in the angular velocity
ωc2
from the point in time t17 to the point in time t20. The imaging angle after the point in time t20 is fixed to
θc4.

As described above, in a case where two threshold values of the angle of the head are provided, in the medical observation system 10, with the fact that the angle of the turning of the head of the surgeon 20 in the left direction exceeds the least threshold value
θTh1
as a trigger point, the video microscope 13 turns at the angular velocity
ωc2
in the right direction which corresponds to the head turning direction, and the imaging angle is changed. Then, in a case where the angle of the head turning of the surgeon 20 exceeds the threshold value
θTh2
other than the threshold value
θTh1,
with the above-described fact as a trigger point, the angular velocity of the turning of the video microscope 13 in the right direction is changed to the angular velocity
ωc3
from the angular velocity
ωc2.

After the head of the surgeon 20 turns in the left direction, the head of the surgeon 20 conversely turns in the right direction, and when the angle of the turning from the original position becomes smaller than the threshold value
θTh2,
with the above-described fact as a trigger point, the angular velocity of the turning of the video microscope 13 in the right direction is changed to angular velocity
ωc2
from angular velocity
ωc3.

In addition, after the head of the surgeon 20 turns in the left direction, the head of the surgeon 20 conversely turns in the right direction, and when the angle of the turning from the original position becomes smaller than the threshold value
θTh1,
with the above-described fact as a trigger point, the video microscope 13 stops the turning and the imaging angle is fixed.

In FIGS. 10A to 10D, the case where the surgeon 20 turns his/her head in the left direction is described. However, even in a case where the surgeon turns his/her head in the right direction, the processing is the same except that the point that the direction of the turning of the video microscope 13 is in is a left direction. In addition, regarding the case where the surgeon 20 vertically moves his/her head, the processing is the same as the case where the head turns horizontally except the point that the imaging angle is at is a vertical angle. In a case where the surgeon 20 turns his/her head both in the vertical direction and the horizontal direction simultaneously, the processes in the cases where the head turns in the horizontal direction and in the vertical direction are performed simultaneously.

In addition, in the example in FIGS. 10A to 10D, the number of threshold values is two. However, the number threshold values may be more than two. The number obtained by adding one to the number of threshold values is the number of types of the angular velocity of the imaging angle (including the angular velocity zero).

As described above, the electric arm 12 changes the imaging angle of the video microscope 13 without changing the distance between the video microscope 13 and the gazing point, based on the angular velocity of the head of the surgeon 20 and the focus area information. Therefore, the surgeon 20 can change the imaging angle of the video microscope 13 by himself by turning his/her head. In addition, since the distance between the video microscope 13 and the gazing point has not changed, even though the imaging angle has changed, it is possible to maintain the focused state. As a result, the surgeon 20 can obtain a focused image of the imaging angle intended by the surgeon 20, and the surgical operation efficiency is improved.

<Second Embodiment>

(Configuration Example of a Medical Observation System in a Second Embodiment

Figure 11:
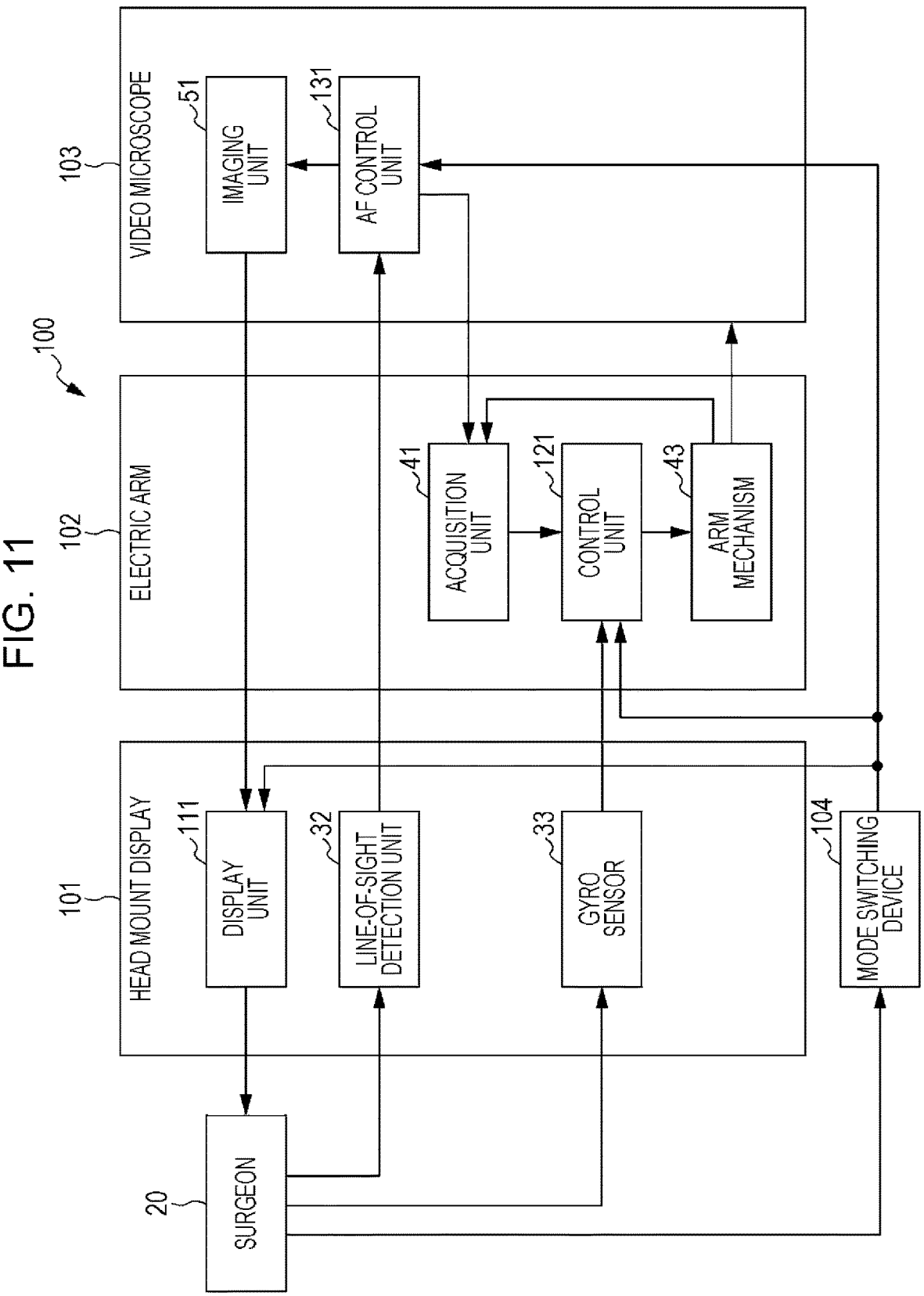
FIG. 11 is a block diagram illustrating a configuration example of a medical observation system in a second embodiment as the imaging control system to which the present disclosure is applied.

FIG. 11 is a block diagram illustrating a configuration example of a medical observation system in a second embodiment as an imaging control system to which the present disclosure is applied.

In the configuration illustrated in FIG. 11, the configuration the same as that in FIG. 2 will be referenced by the same reference signs. The duplicated descriptions will be appropriately omitted.

A medical observation system 100 in FIG. 11 is configured to include a head mount display 101, an electric arm 102, a video microscope 103, and a mode switching device 104. In the medical observation system 100, a control mode that controls the imaging angle and the focus area as operation modes can be set, and only in a case where the operation mode is the control mode, the imaging angle and the focus area is changed.

Specifically, a configuration of the head mount display 101 of the medical observation system 100 is different from that of the head mount display 11 in FIG. 2 in the point that a display unit 111 is provided instead of the display unit 31 is included.

The display unit 111 of the head mount display 101 displays an imaged image transmitted from the video microscope 103. In addition, the display unit 111 causes mode information which indicates the operation mode transmitted from the mode switching device 104 to be displayed. It is desirable that the mode information is displayed at the recognizable location without moving the line-of-sight of the surgeon 20.

A configuration of the electric arm 102 is different from that of the electric arm 12 in FIG. 2 in the point that a control unit 121 instead of the control unit 42 is included.

The control unit 121 of the electric arm 102 acquires the operation mode from the mode switching device 104. In a case where the operation mode is the control mode, the control unit 121 acquires the detection result transmitted from the gyro sensor 33. In a case where the operation mode is the control mode, the control unit 121 controls the arm mechanism 43 such that the imaging angle of the video microscope 103 is changed without changing the distance between the video microscope 103 and the gazing point, based on the acquired detection result and the focus area information from the acquisition unit 41.

A configuration of the video microscope 103 is different from that of the video microscope 13 in FIG. 2 in the point that an AF control unit 131 is provided instead of the AF control unit 52.

The AF control unit 131, when the imaging starts, sets the predetermined area such as the center area of the imaged image as the focus area. In addition, in a case of the time other than starting imaging and in a case where the operation mode transmitted from the mode switching device 104 is the control mode, the AF control unit 131 sets the position indicated by the gazing point position information transmitted from the head mount display 101 as the focus area.

The AF control unit 131 controls the focusing of the imaging unit 51 such that the image focuses on the focus area by a detection method such as a contrast detection system or a phase difference detection system. In association with this, the AF control unit 131 detects the distance between the video microscope 103 and the object in the focus area, and transmits the distance information indicating the detected distance to the electric arm 102.

The mode switching device 104, for example, is formed of a photo switch. The surgeon 20 instructs to switch the control mode and non-control mode by operating the mode switching device 104 by a foot or the like. The non-control mode is a mode in which the control of imaging angle and the focus area are not performed.

The mode switching device 104 sets the operation mode to the control mode or the non-control mode according to the instruction from the surgeon 20. The mode switching device 104 supplies the set operation mode to the head mount display 101, electric arm 102, and the video microscope 103.

The imaging angle control processing of the medical observation system 100 is similar to the imaging angle control processing in FIG. 9 except the point that the processing is performed in a case where the operation mode is the control mode and the point that the mode information which indicates that the operation mode is the control mode is displayed on the display unit 111.

Since the electric arm 102 of the medical observation system 100 performs the imaging angle control processing only in a case where operation mode is the control mode, compared to a case where the imaging angle control and the focus area control are performed at all time, it is possible to reduce the tension and the tiredness of the surgeon 20.

That is, in a case where the imaging angle control and the focus area control are performed at all times, the surgeon 20 has to move his/her head and the line-of-sight with a constant awareness at all times, and thus, there is possibility of causing excessive tension and tiredness. However, in the medical observation system 100, since the operation mode can be set, in a case where the imaging angle control and the focus area control are not necessary, the surgeon 20 does not have to be aware of the head movement or the line-of-sight by setting the operation mode to the non-control mode. As a result, it is possible to reduce the tension and the tiredness of the surgeon 20.

In a case where the operation mode is non-control mode, the imaging unit 51 of the video microscope 103 performs the imaging such that the image focuses on the present focus area at the present imaging angle. Then, the display unit 111 of the head mount display 101 displays the imaged image obtained as the result of above-described imaging together with the mode information which indicates the fact that the operation mode is the non-control mode.

<Third Embodiment>

(Configuration Example of a Medical Observation System in a Third Embodiment)

Figure 12:
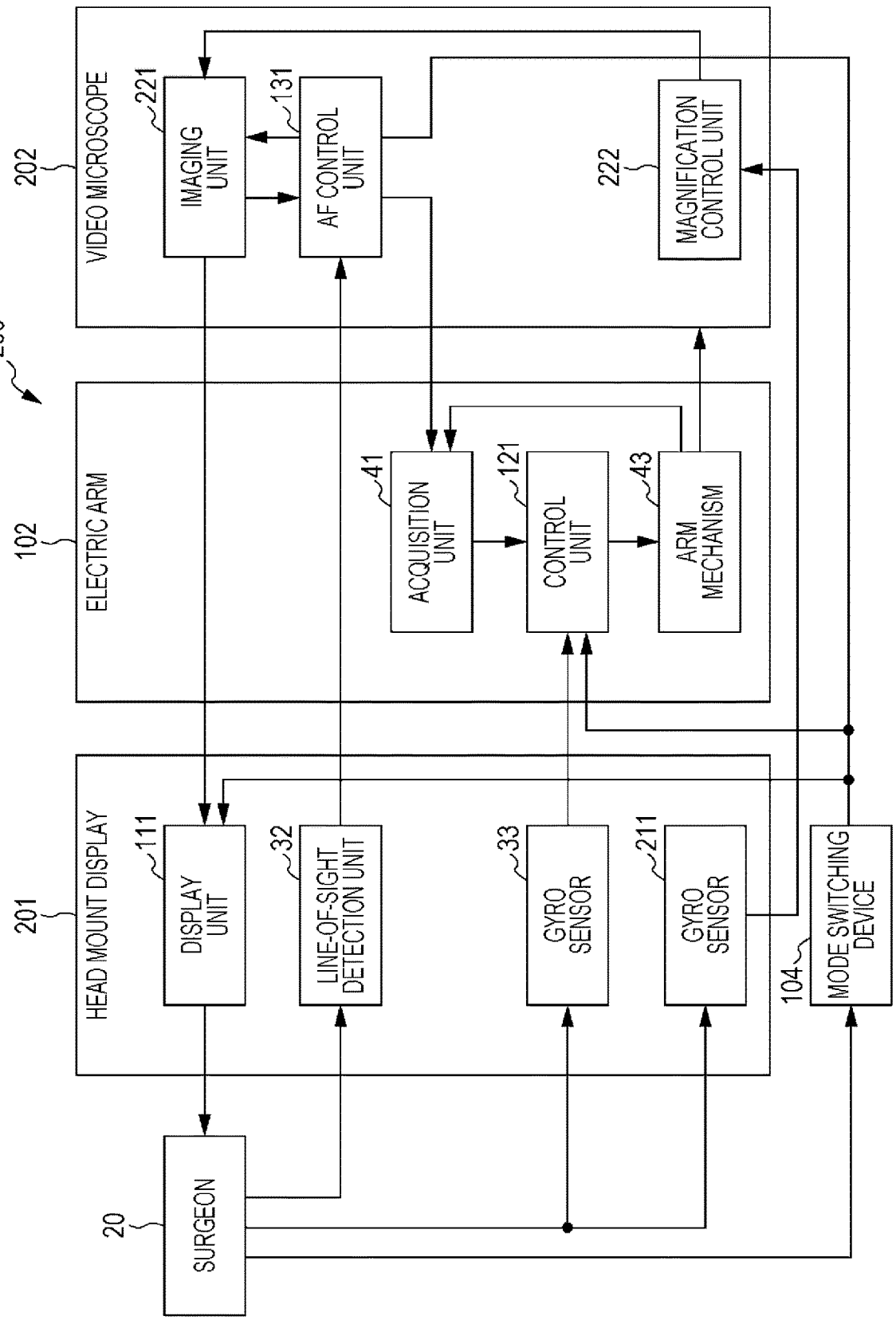
FIG. 12 is a block diagram illustrating a configuration example of a medical observation system in a third embodiment as the imaging control system to which the present disclosure is applied.

FIG. 12 is a block diagram illustrating a configuration example of a medical observation system in a third embodiment as an imaging control system to which the present disclosure is applied.

In the configuration illustrated in FIG. 12, the configurations the same as those in FIG. 2 and FIG. 11 will be referenced by the same reference signs. The duplicated descriptions will be appropriately omitted.

A configuration of a medical observation system 200 in FIG. 12 is different from that of the configuration of a medical observation system 100 in FIG. 11 in the point that a head mount display 201 is provided instead of the head mount display 101 and the video microscope 202 is provided instead of the video microscope 103. The medical observation system 200 changes the imaging magnification of the video microscope 202 according to the horizontal inclination of the head of the surgeon 20.

Specifically, the head mount display 201 of the medical observation system 200 is different from the head mount display 101 in FIG. 11 in the point that a new gyro sensor 211 is provided.

The gyro sensor 211 is a gyro sensor of one axis and detects the angular velocity of the horizontal inclination of the head of the surgeon 20. The gyro sensor 211 transmits the detection result to the video microscope 202.

The video microscope 202 is different from the video microscope 103 in FIG. 11 in the point that an imaging unit 221 is provided instead of the imaging unit 51 and a new magnification control unit 222 is provided.

The imaging unit 221 performs the imaging at the imaging magnification supplied from the magnification control unit 222 based on the focus control of the AF control unit 131 and transmits the imaged image obtained as a result of imaging to the head mount display 201.

The magnification control unit 222 determines the imaging magnification of the imaging unit 221 according to the detection result transmitted from the gyro sensor 211, and supplies the imaging magnification to the imaging unit 221.

In the third embodiment, the magnification control unit 222 is included in the video microscope 202. However, the magnification control unit 222 may be included in the electric arm 102.

(Example of the Head Movement of the Surgeon when the Imaging Magnification is Changed)

Figure 13:
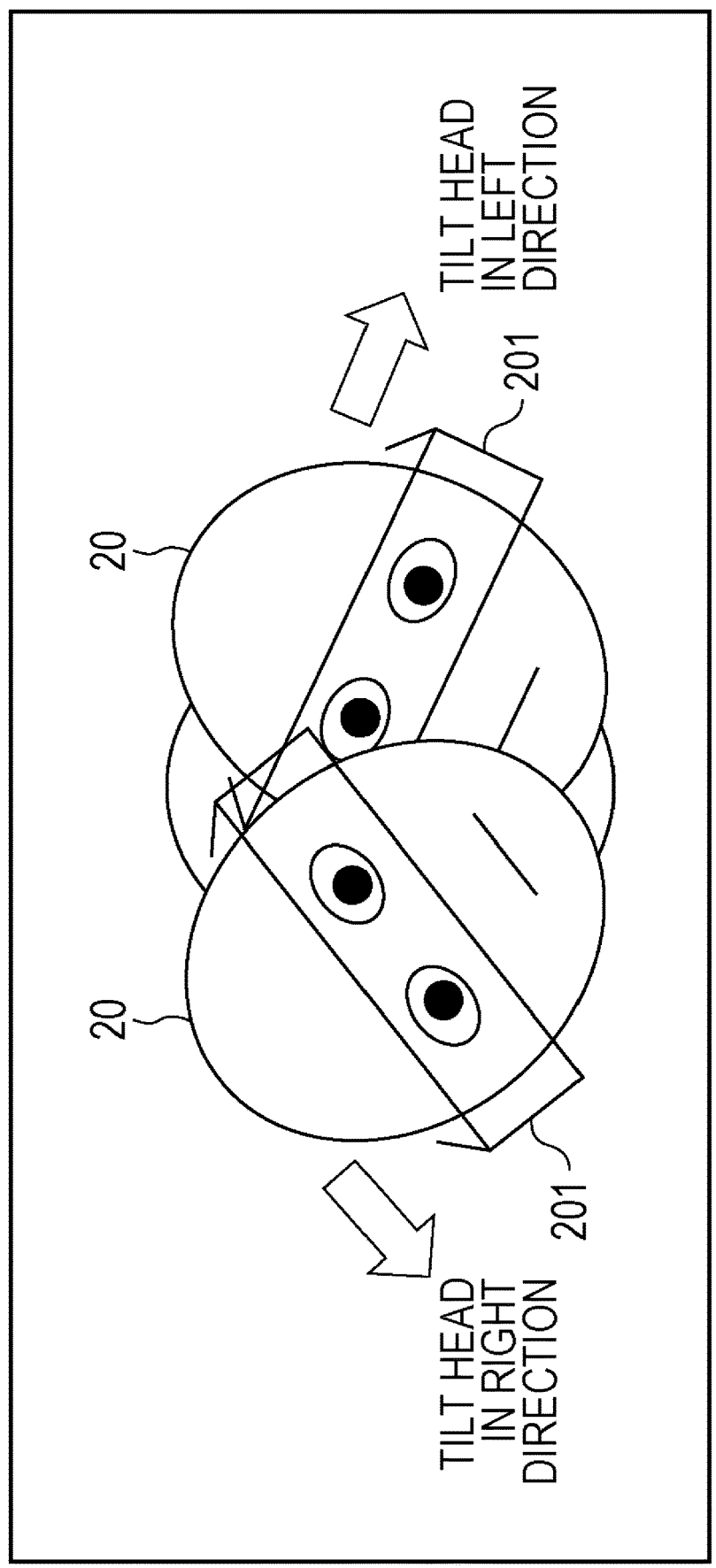
FIG. 13 is a diagram illustrating a head movement of the surgeon when an imaging magnification is changed.
Figure 14:
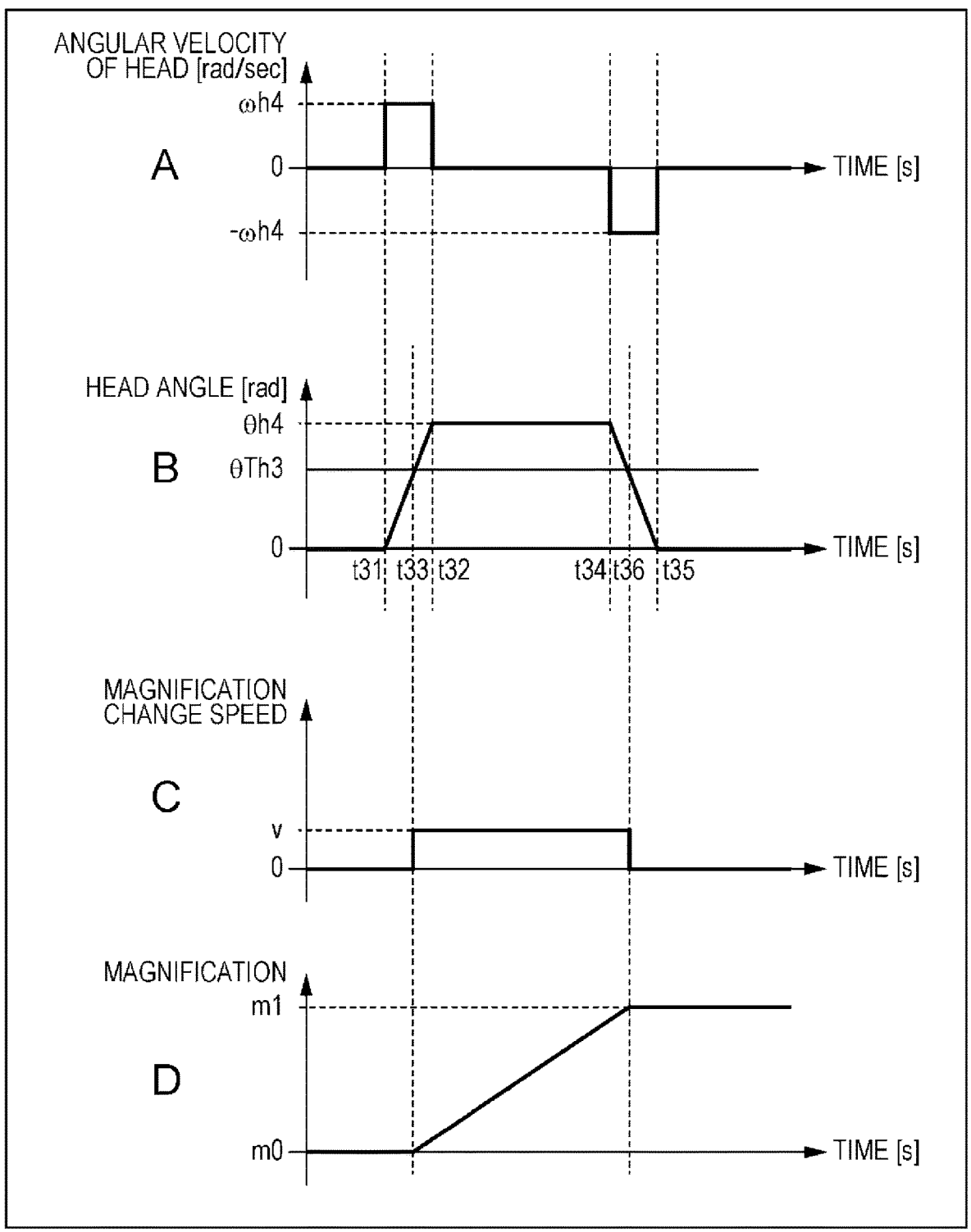
FIG. 14 is a diagram illustrating an example of a temporal change of an angular velocity of the head turning and the imaging magnification.

FIG. 13 is a diagram illustrating a head movement of the surgeon 20 when the imaging magnification of the video microscope 13 is changed.

As illustrated in FIG. 13, when changing the imaging magnification of the video microscope 202, the surgeon 20 tilts his/her head in the horizontal direction in a state of wearing the head mount display 201. That is, the surgeon 20 wearing the head mount display 201, when changing the imaging magnification of the video microscope 202, turns his/her head in a different direction from the direction in the case of turning the head when changing the imaging angle. In this way, in the medical observation system 200, it is possible to control the imaging magnification independent of the imaging angle.

In a case where the surgeon 20 tilts the head in the right direction, the imaging magnification increases (moves toward the telephoto side). On the other hand, in a case where the surgeon 20 tilts the head in the left direction, the imaging magnification decreases (moves toward the wide-angle side). The angular velocity of the head tilting of the surgeon 20 is detected by the gyro sensor 211.

A relationship between the head movement of the surgeon 20 and the imaging magnification is not limited to the example described above.

(Example of a Temporal Change of the Angular Velocity of the Head and the Imaging Magnification)

FIGS. 14A to 14D are diagrams illustrating an example of a temporal change of the angular velocity of the head tilting and the imaging magnification of the video microscope 103 detected by the gyro sensor 211.

In the example in FIGS. 14A to 14D, in order to increase the imaging magnification, the surgeon 20 tilts his/her head at a constant speed in the right direction from a point in time t31, and stops tilting at a point in time t32 when the head tilt becomes a predetermined tilt angle. In this way, as illustrated in FIG. 14A, the gyro sensor 211 detects the angular velocity $\omega h4$ from the point in time t31 to the point in time t32, and transmits the angular velocity $\omega h4$ to the magnification control unit 222.

The magnification control unit 222 acquires the angular velocity $\omega h4$ from the time at point t31 to the time at point t32 from the gyro sensor 211. The magnification control unit 222 measures the angle of the head tilt of the surgeon 20 at the present point in time by integrating the angular velocity acquired from the point in time t31 to the present point in time. The angle measured in this way increases from zero to $\theta h4$ with a predetermined slope from the point in time t31 to the point in time t32 as illustrated in FIG. 14B.

As illustrated in FIG. 14C, the magnification control unit 222 starts the increasing of the imaging magnification at the point in time t33 when the measured angle exceeds the threshold value $\theta Th3 (\theta Th3 < \theta h4)$ at a speed v.

The surgeon 20, after the point in time t32, does not move his/her head until the imaging angle of the video microscope 103 is close to the desired imaging angle, and at the point in time t34, when the imaging angle of the video microscope 103 is close to the desired imaging angle, tilts his/her head at the constant velocity in the left direction. As a result, at the point in time t35, the head of the surgeon 20 returns to the original position and then, the surgeon 20 stops the tilting of the head.

In this way, as illustrated in FIG. 14A, the gyro sensor 211 detects the angular velocity 0 from the point in time t32 to the point in time t34, and transmits the angular velocity 0 to the magnification control unit 222. In addition, the gyro sensor 211 detects the angular velocity $-\omega h4$ from the point in time t34 to the point in time t35, and transmits the angular velocity $-\omega h4$ to the magnification control unit 222.

The magnification control unit 222 acquires the angular velocity 0 from the gyro sensor 211 from the point in time t32 to the point in time t34. The magnification control unit 222 measures the angle of the head tilt of the surgeon 20 at the present point in time by integrating the angular velocity acquired from the point in time t31 to the present point in time. The angle measured in this way is the angle $\theta h4$ from the point in time t32 to the point in time t34 as illustrated in FIG. 14B.

In addition, the magnification control unit 222 acquires the angular velocity $-\omega h4$ from the gyro sensor 211 from the point in time t34 to the point in time t35. The magnification control unit 222 measures the angle of the head tilt of the surgeon 20 at the present point in time by integrating the angular velocity acquired from the point in time t31 to the present point in time. The angle measured in this way decreases from $\theta h4$ to zero with a predetermined slope from the point in time t34 to the point in time t35 as illustrated in FIG. 14B.

As illustrated in FIG. 14C, in the point in time t36 when the measured angle becomes equal to or less than the threshold value $\theta Th3$, the magnification control unit 222 makes the speed of the changing of the imaging magnification to be zero, and stops changing the imaging magnification.

In this way, the imaging magnification is changed at the speed v from the point in time t33 to the point in time t36. As a result, as illustrated in FIG. 14D, the imaging magnification increases from imaging magnification m0 which is the imaging magnification before the head is tilted to imaging magnification m1 at the speed v from the point in time t33 to the point in time t36. After the point in time t36, the imaging magnification is fixed to the imaging magnification m1.

As described above, in the medical observation system 200, by using the tilting of the head of the surgeon 20 in the right direction as a trigger point, the imaging magnification is changed in the direction of increasing corresponding to the direction of tilting. After that, by using the tilting of the head of the surgeon 20 in the left direction reverse to the previous direction as a trigger point, the imaging magnification stops changing, and the imaging magnification is fixed.

In FIGS. 14A to 14D, the case where the surgeon 20 tilts his/her head in the right direction is described. However, in a case where the surgeon tilts his/her head in the left direction also, the processing is the same except the point at which the direction of the changing of the imaging magnification is the direction of the decreasing.

(Description of the Processing of the Medical Observation System)

Figure 15:
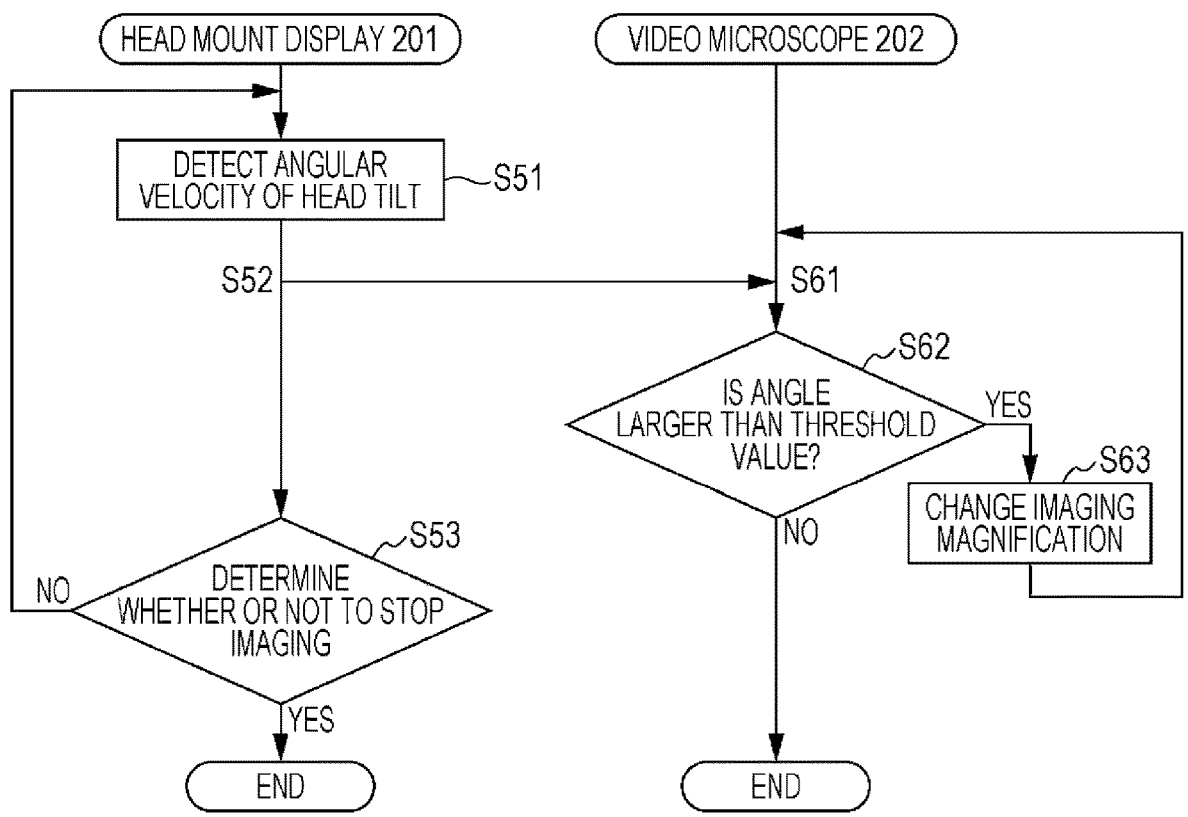
FIG. 15 is a flow chart explaining imaging magnification control processing of the medical observation system in FIG. 12.
Figure 16:
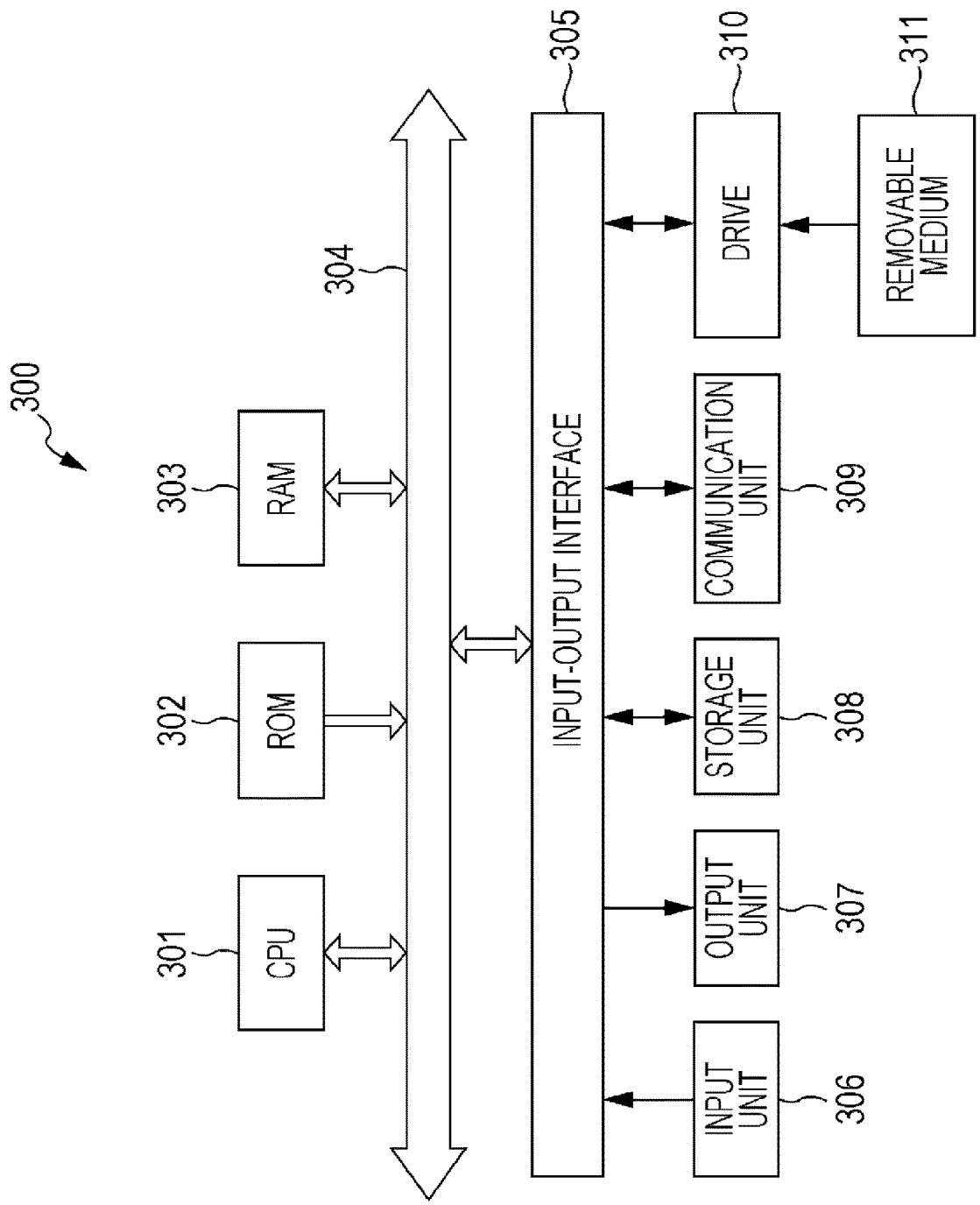
FIG. 16 is a block diagram illustrating an example of a hardware configuration of a computer.

FIG. 15 is a flow chart explaining imaging magnification control processing of the medical observation system 200 in FIG. 12. The imaging magnification control processing, for example, starts when the imaging unit 51 starts imaging in the imaging angle control processing.

In STEP S51 in FIG. 15, the gyro sensor 211 of the head mount display 201 detects the angular velocity of the head tilt of the surgeon 20. In STEP S52, the gyro sensor 211 transmits the detection result to the video microscope 202.

In STEP S61, the magnification control unit 222 of the video microscope 202 acquires the detection result transmitted from the gyro sensor 211. In STEP S62, the magnification control unit 222 integrates the angular velocity of the head tilt which is the acquired detection result, and determines whether the angle of the head tilt obtained from the detection result is larger than the threshold value θTh3 or not. In a case where the angle of the head tilt is determined to be larger than the threshold value θTh3 in STEP S61, that is, in a case where the surgeon 20 tilts his/her head in the direction corresponding to the desired imaging magnification, the process proceeds to STEP S63.

In STEP S63, the magnification control unit 222 changes the imaging magnification in the direction corresponding to the direction of the head tilt at the predetermined speed v, and the process returns to STEP S61.

On the other hand, in a case where the angle of the head tilt is determined not to be larger than the threshold value θTh3 in STEP S62, that is, in a case where the surgeon 20 returns his/her head to the original position, or in a case where the surgeon 20 does not tilt his/her head, the process ends.

In STEP S53, the head mount display 201 determines whether or not the imaging unit 221 stops imaging in the imaging angle control processing. In a case where the imaging unit 221 determines not to stop imaging in STEP S53, the process returns to STEP S51 and repeats the subsequent processes.

On the other hand, in a case where the imaging unit 221 determines to stop imaging in STEP S53, the process ends.

The imaging angle control processing of the medical observation system 200 is similar to the imaging angle control processing in FIG. 9 except the point at which the imaging angle control processing is performed in a case where the operation mode is the control mode and the point that mode information which indicates that the operation mode is the control mode is displayed on the display unit 111.

The medical observation system 200 may be configured so as to perform the imaging magnification control processing only in a case where the operation mode is the control mode. In this case, the control mode set by the mode switching device 104 is a mode that controls the imaging angle, the focus area, and the imaging magnification, and the non-control mode is a mode that does not control the imaging angle, the focus area, and the imaging magnification.

In addition, the operation mode may not be set as a common mode for all of the imaging angle, the focus area, and the imaging magnification, but may be set as an individual mode. In this case, only in a case where the operation mode of the imaging angle is the control mode for controlling the imaging angle, the imaging angle is controlled according to the vertical and horizontal head turning of the surgeon 20. In addition, only in a case where the operation mode of the focus area is the control mode for controlling the focus area, is the focus area controlled according to the line-of-sight of the surgeon 20. Furthermore, only in a case where the operation mode of the imaging magnification is the control mode for controlling the imaging magnification, is the imaging magnification controlled according to the horizontal head tilt of the surgeon 20.

Furthermore, the threshold value of the angle of the head tilt also, as similar to the threshold value of the angle of the head turning illustrated in FIGS. 10A to 10D, may be provided in plural. In this case, it is possible to change the changing speed of the imaging magnification.

In the first to third embodiments, the angle of head turning or head tilt is used as the trigger point in the control of the imaging angle or the imaging magnification. However, the value itself corresponding to the angle of head turning or head tilt may be set as the imaging angle and the imaging magnification.

<Fourth Embodiment>

(Description of a Computer to Which the Present Disclosure is Applied)

The series of processing described above can be executed by hardware and can also be executed by software. In a case where the series of processing is executed by software, a program that configures the software is installed to a computer. Here, in the computer, a computer which is incorporated in the dedicated hardware and, for example, a general-purpose personal computer which is capable of executing various functions by installing various programs, are included.

FIG. 16 is a block diagram illustrating an example of a hardware configuration of a computer that executes the series of processing by the program.

In a computer 300, a central processing unit (CPU) 301, a read only memory (ROM) 302, and a random access memory (RAM) 303 are connected to each other by a bus 304.

An input-output interface 305 is further connected to the bus 304. An input unit 306, an output unit 307, a storage unit 308, a communication unit 309, and a drive 310 are connected to the input-output interface 305.

The input unit 306 is formed of a keyboard, a mouse, a microphone, and the like. The output unit 307 is formed of a head mount display, a speaker, and the like. The storage unit 308 is formed of a hard disk, a non-volatile memory, and the like. The communication unit 309 is formed of a network interface, and the like. The drive 310 drives a magnetic disk, an optical disk, or a removable medium 311 such as a semiconductor memory.

In the computer 300 configured as described above, the series of processing described above is performed by the CPU 301, for example, causing the program stored in the storage unit 308 to be loaded on the RAM 303 and to be executed, via the input-output interface 305 and the bus 304.

The program executed by the computer 300 (CPU 301), for example, can be provided by being recorded in the removable medium 311 as a packaged medium or the like. In addition, the program can be provided via a wired or wireless transmission medium such as a local area network, the internet, or digital satellite broadcasting.

In the computer 300, by mounting the removable medium 311 on the drive 310, the program can be installed in the storage unit 308 via the input-output interface 305. In addition, the program can be received by the communication unit 309 via the wired or the wireless transmission medium, and can be installed in the storage unit 308. Otherwise, the program can be stored in the ROM 302 or the storage unit 308 in advance.

The program executed by the computer 300 may be a program in which the processing is performed sequentially in the order described in the present Specification, or may be a program in which the processing is performed in parallel or at the necessary timing when a call occurs.

In addition, in the present Specification, the system means a collection of a plurality of configuration components (device, a module (component), and the like), and it does not matter whether all of the configuration components are in the same housing. Therefore, both of a plurality of devices accommodated in the individual housing and connected to each other via a network and one device in which a plurality of modules are accommodated in one housing are the system.

The effects disclosed in the present Specification are illustrative examples only, but not limited thereto, and there may be other effects.

In addition, the embodiments in the present disclosure are not limited to the embodiments described above, and various modifications can be made without departing from the scope of the present disclosure.

The present disclosure can be can be configured as follows.

(1)
A surgical control device including:
circuitry configured to change an imaging viewpoint of a surgical imaging device in order to maintain a substantially constant distance between a focal point of an object and the surgical imaging device that images the object, based on a first instruction of a user and position information acquired by an acquisition unit implemented by circuitry configured to acquire position information indicating a position of the focal point of the object.

(2)
The surgical control device according to above (1) in which the circuitry is further configured to change an imaging magnification of the surgical imaging device according to a second instruction of the user.

(3)
The surgical control device according to above (2) in which the first instruction corresponds to a first movement and the second instruction corresponds to a second movement, and
a direction of the first movement and a direction of the second movement are different from each other.

(4)
The surgical control device according to any one of above (1) to (3) in which the circuitry is further configured to change the imaging viewpoint based on the first instruction, which is a movement of a head of the user and the position information.

(5)
The surgical control device according to any one of above (1) to (4) in which the circuitry is further configured to change the imaging viewpoint based on an angular velocity indicating the first instruction, which is a movement of a head of the user and the position information.

(6)
The surgical control device according to any one of above (1) to (5) in which the circuitry is further configured to change the imaging viewpoint in a case where an operation mode is a predetermined mode.

(7)
The surgical control device according to any one of above (1) to (6) in which the position information is determined based on a gazing point of the user.

(8)
The surgical control device according to any one of above (1) to (7), further including a holding unit that holds the imaging device so as to freely move and turn, in which the circuitry is further configured to change the imaging viewpoint of the surgical imaging device by controlling the holding device.

(9)
A control method including: in a control device,
changing, using a surgical control device, an imaging viewpoint of a surgical imaging device in order to maintain a substantially constant distance between a focal point of an object and the surgical imaging device that images the object based on a first instruction of a user and the position information acquired by a process of the acquiring position information indicating a position of the focal point of the object.

(10)
An imaging control system including:
a surgical imaging device that images an object; and
a surgical imaging control device including circuitry configured to change an imaging viewpoint of a surgical imaging device in order to maintain a substantially constant distance between a focal point of an object and the surgical imaging device that images the object, based on an instruction of a user and position information acquired by an acquisition unit implemented by circuitry configured to acquire position information indicating a position of the focal point of the object.

(11)
The imaging control system according to above (10), further including:
a detection device that detects the movement.

(12)
The imaging control system according to above (11) in which the detection device is a head mount display for the user to wear.

(13)
The imaging control system according to above (11) to (12) in which the head mount display includes further circuitry configured to
detect the movement and
detect a gazing point of the user,
wherein the position information is determined based on the gazing point detected by the further circuitry.

(14)
A control device including:
an acquisition unit that acquires position information indicating a position of an object; and
a control unit that changes an imaging angle of an imaging device without changing a distance between the object and the imaging device that images the object based on a first movement of a user and the position information acquired by the acquisition unit.

(15)
The control device according to above (14), further including:
a magnification control unit that changes an imaging magnification of the imaging device according to a second movement of the user.

(16)

The control device according to above (15) in which a direction of the first movement and a direction of the second movement are different from each other.

(17)

The control device according to any one of above (14) to (16) in which the control unit changes the imaging angle based on the first movement of the head of the user and the position information.

(18)

The control device according to any one of above (14) to (17) in which the control unit changes the imaging angle based on an angular velocity indicating the first movement of the head of the user and the position information.

(19)

The control device according to any one of above (14) to (18) in which the control unit changes the imaging angle in a case where an operation mode is a predetermined mode.

(20)

The control device according to any one of above (14) to (19) in which the position information is determined based on a gazing point of the user.

(21)

The control device according to any one of above (14) to (20), further including a holding unit that holds the imaging device so as to freely move and turn, in which the control unit changes the imaging angle of the imaging device by controlling the holding unit.

(22)

The control device according to any one of above (14) to (21) in which the imaging device is a video microscope for surgical operation.

(23)

A control method including: in a control device, acquiring position information indicating a position of an object; and controlling for changing an imaging angle of an imaging device without changing a distance between the object and the imaging device that images the object based on a first movement of a user and the position information acquired by a process of acquiring.

(24)

An imaging control system including:

an imaging device that images an object; and a control device, in which the control device includes an acquisition unit that acquires position information indicating a position of the object, and a control unit that changes an imaging angle of an imaging device without changing a distance between the object and the imaging device that images the object based on a first movement of a user and the position information acquired by the acquisition unit.

(25)

The imaging control system according to above (24), further including: a detection device that detects the first movement.

(26)

The imaging control system according to above (25) in which the detection device is a head mount display for the user to wear.

(27)

The imaging control system according to above (25) to (26) in which the detection device includes a movement detection unit that detects the first movement and a line-of-sight detection unit that detects a gazing point of the user, in which the position information is determined based on the gazing point detected by the line-of-sight detection unit.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 10 medical observation system
11 head mount display
12 electric arm
13 video microscope
32 line-of-sight detection unit
33 gyro sensor
41 acquisition unit
42 control unit
43 arm mechanism
100 medical observation system
101 head mount display
102 electric arm
103 video microscope
121 control unit
200 medical observation system
201 head mount display
202 video microscope
222 magnification control unit

The invention claimed is:

1. A surgical control device comprising:
   circuitry configured to:
      obtain a surgical image from a surgical imaging device supported by an electric arm, gazing information of a user that watches a display of the surgical image including a gazing point, and first head movement information indicating a movement of the user's head, and
      change, by controlling the electric arm, an imaging viewpoint of the surgical imaging device, based on the obtained gazing information and first head movement information, wherein the circuitry is further configured to change the imaging viewpoint based on the first head movement when the gazing point is on the surgical image.

2. The surgical control device according to claim 1, wherein the circuitry is further configured to change an imaging magnification of the surgical imaging device according to obtained second head movement information.

3. The surgical control device according to claim 2, wherein a first direction associated with the first head movement information and a second direction associated with the second head movement information are different from each other.

4. The surgical control device according to claim 1, wherein the change of the imaging view point corresponds to a change in a position of the surgical imaging device, and wherein the circuitry is further configured to change the position of the surgical imaging device based on the first head movement information.

5. The surgical control device according to claim 1, wherein the change of the imaging view point corresponds to a change in a position of the surgical imaging device, and wherein the circuitry is further configured to change the position of the surgical imaging device based on the first head movement information including an angular velocity associated with a movement of the head of the user.

6. The surgical control device according to claim 1, wherein the change of the imaging view point corresponds to a change in a position of the surgical imaging device, and wherein the circuitry is further configured to change the position of the surgical imaging device in a case where an operation mode is a predetermined mode.

7. The surgical control device according to claim 1, wherein the circuitry is further configured to:
- detect an angular velocity at least indicating a vertical head movement of the user, and
- change, by controlling the electric arm, the imaging viewpoint of the surgical imaging device, based on the obtained gazing information and first head movement information, wherein the electric arm, based on the detected angular velocity, changes the imaging angle of the surgical imaging device without changing a distance between the surgical imaging device and the gazing point.

8. A control method comprising:
- obtaining a surgical image from a surgical imaging device supported by an electric arm, gazing information of a user watching a display displaying the surgical image including a gazing point, and first head movement information indicating a movement of the user's head; and
- changing, by controlling the electric arm, an imaging viewpoint of the surgical imaging device, based on the obtained gazing information and first head movement information, wherein the imaging viewpoint of the surgical imaging device is changed based on the first head movement when the gazing point is on the surgical image.

9. An imaging control system comprising:
- a surgical imaging device that images an object;
- a user imaging device that images a user; and
- a surgical imaging control device including circuitry configured to:
  - obtain a surgical image from the surgical imaging device supported by an electric arm, gazing information of the user that watches a display of the surgical image including a gazing point, and first head movement information indicating a movement of the user's head, and
  - change, by controlling the electric arm, an imaging viewpoint of the surgical imaging device, based on the obtained gazing information and first head movement information, wherein the circuitry is further configured to change the imaging viewpoint of the surgical imaging device based on the first head movement when the gazing point is on the surgical image.

10. The imaging control system according to claim 9, wherein the user imaging device is configured to generate a head image of the user, and wherein the circuitry is further configured to generate the first head movement information based on the head image.

\* \* \* \* \*